United States Patent
Lee et al.

(10) Patent No.: US 10,755,453 B2
(45) Date of Patent: Aug. 25, 2020

(54) IMAGE PROCESSING APPARATUS, IMAGE PROCESSING METHOD, AND ULTRASOUND IMAGING APPARATUS HAVING IMAGE PROCESSING UNIT

(71) Applicant: SAMSUNG ELECTRONICS CO., LTD., Suwon-si (KR)

(72) Inventors: Kyong Joon Lee, Seongnam-si (KR); Won-chul Bang, Seongnam-si (KR); Youngtaek Oh, Seoul (KR); Jiwon Ryu, Suwon-si (KR); Jayeon Jeong, Yongin-si (KR)

(73) Assignee: SAMSUNG ELECTRONICS CO., LTD., Suwon-si (KR)

(*) Notice: Subject to any disclaimer, the term of this patent is extended or adjusted under 35 U.S.C. 154(b) by 0 days.

(21) Appl. No.: 14/862,448

(22) Filed: Sep. 23, 2015

(65) Prior Publication Data
US 2016/0125605 A1     May 5, 2016

(30) Foreign Application Priority Data

Oct. 29, 2014 (KR) .................... 10-2014-0148242

(51) Int. Cl.
*G06T 11/00* (2006.01)
*A61B 6/00* (2006.01)
(Continued)

(52) U.S. Cl.
CPC ............ *G06T 11/008* (2013.01); *A61B 6/032* (2013.01); *A61B 6/463* (2013.01); *A61B 6/5247* (2013.01); *A61B 6/541* (2013.01); *A61B 8/085* (2013.01); *A61B 8/5261* (2013.01); *G06T 7/33* (2017.01); *A61B 8/4405* (2013.01); *G01R 33/4812* (2013.01); *G01R 33/4814* (2013.01); *G06T 2207/10016* (2013.01); *G06T 2207/10081* (2013.01); *G06T 2207/10088* (2013.01);
(Continued)

(58) Field of Classification Search
None
See application file for complete search history.

(56) References Cited

U.S. PATENT DOCUMENTS 6,804,683 B1* 10/2004 Matsuzaki ........ G06F 17/30256
2013/0223716 A1* 8/2013 Mori .................... A61B 5/0013
                                                                    382/131

(Continued)

OTHER PUBLICATIONS

Marx M, Ehrhardt J, Werner R, Schlemmer HP, Handels H. Simulation of spatiotemporal CT data sets using a 4D MRI-based lung motion model. International journal of computer assisted radiology and surgery. May 1, 2014;9(3):401-9.*

(Continued)

*Primary Examiner* — Vu Le
*Assistant Examiner* — Tracy Mangialaschi
(74) *Attorney, Agent, or Firm* — Sughrue Mion, PLLC

(57) ABSTRACT

An image processing apparatus includes an input device configured to receive a computerized tomography image of a first respiration phase of an object; a data selector configured to select magnetic resonance image data similar to the object from among magnetic resonance image data; and an image generator configured to generate a computerized tomography image of a second respiration phase of the object based on the selected magnetic resonance image data.

20 Claims, 15 Drawing Sheets

(51) Int. Cl.
G06T 7/33 (2017.01)
A61B 8/08 (2006.01)
A61B 6/03 (2006.01)
A61B 8/00 (2006.01)
G01R 33/48 (2006.01)

(52) U.S. Cl.
CPC ............ G06T 2207/10132 (2013.01); G06T 2211/412 (2013.01)

(56) References Cited

U.S. PATENT DOCUMENTS

2014/0212013 A1* 7/2014 Han .................. G06T 5/007 382/131
2017/0053064 A1* 2/2017 Bhavani .............. G06Q 50/22

OTHER PUBLICATIONS

Blackall, Jane M., et al. "Alignment of sparse freehand 3-D ultrasound with preoperative images of the liver using models of respiratory motion and deformation." IEEE transactions on medical imaging 24.11 (2005): 1405-1416.*

Boye, Dirk, Tony Lomax, and Antje Knopf. "Mapping motion from 4D-MRI to 3D-CT for use in 4D dose calculations: a technical feasibility study." Medical physics 40.6 (2013): 061702.*

Möller, Manuel, et al. "Medical Image Understanding Through the Integration of Cross-Modal Object Recognition with Formal Domain Knowledge." HEALTHINF (1). 2008.*

Robinson, G. P., et al. "Medical image collection indexing: shape-based retrieval using KD-trees." Computerized Medical Imaging and Graphics 20.4 (1996): 209-217.*

Gudivada, Venkat N., and Vijay V. Raghavan. "Content based image retrieval systems." Computer 28.9 (1995): 18-22.*

Shi, Rong, and Hartmut Derendorf. "Pediatric dosing and body size in biotherapeutics." Pharmaceutics 2.4 (2010): 389-418.*

Bosy-Westphal, A., et al. "Effect of organ and tissue masses on resting energy expenditure in underweight, normal weight and obese adults." International journal of obesity 28.1 (2004): 72.*

Müller, Manfred J., et al. "Effect of constitution on mass of individual organs and their association with metabolic rate in humans—a detailed view on allometric scaling." PloS one 6.7 (2011): e22732.*

Liu, Yanxi, William E. Rothfus, and Takeo Kanade. "Content-based 3d neuroradiologic image retrieval: Preliminary results." Proceedings 1998 IEEE International Workshop on Content-Based Access of Image and Video Database. IEEE, 1998. (Year: 1998).*

Kim, Jinman, et al. "A new way for multidimensional medical data management: Volume of interest (VOI)-based retrieval of medical images with visual and functional features." IEEE Transactions on Information Technology in Biomedicine 10.3 (2006): 598-607. (Year: 2006).*

Cai, Tom Weidong, Jinman Kim, and David Dagan Feng. "Content-based medical image retrieval."; Biomedical information technology. Academic Press, 2008. 83-113. (Year: 2008).*

Boye, Dirk, et al. "Population based modeling of respiratory lung motion and prediction from partial information."; Medical Imaging 2013: Image Processing. vol. 8669. International Society for Optics and Photonics, 2013. (Year: 2013).*

* cited by examiner (a)            (b)

FIG. 5
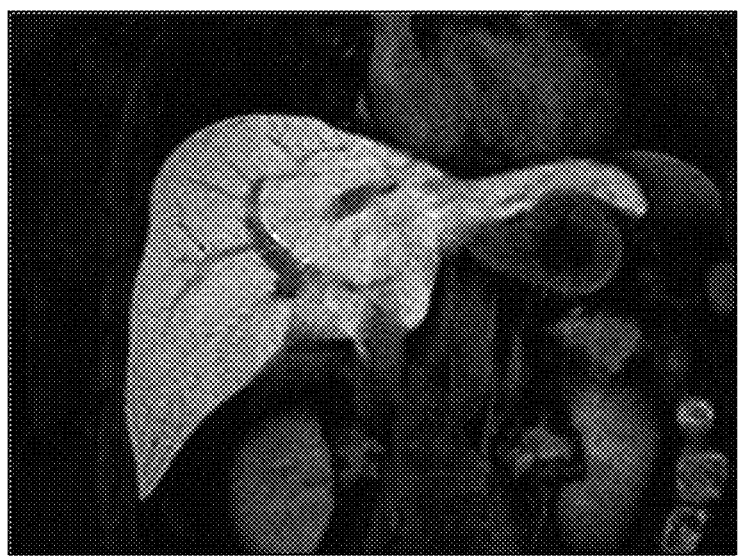
(a)
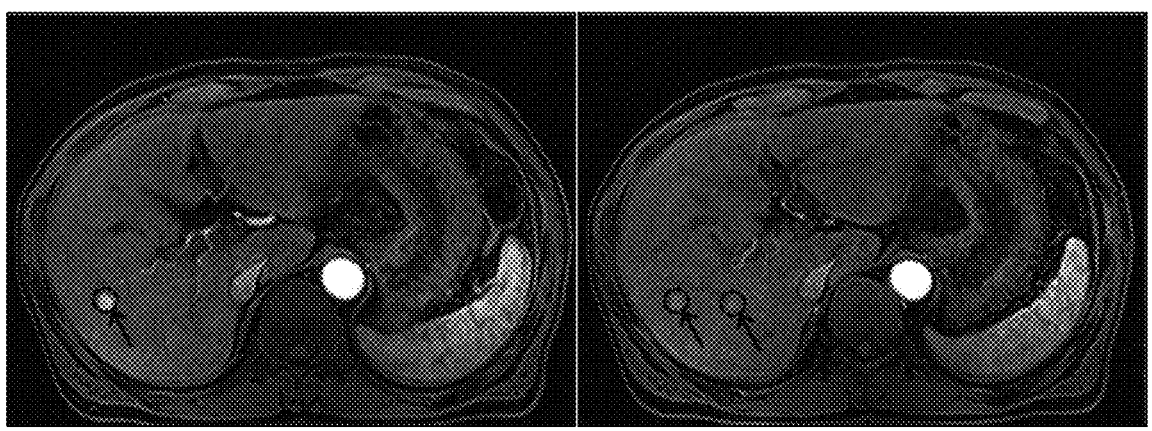
(b)

FIG. 6
(a) INHALATION
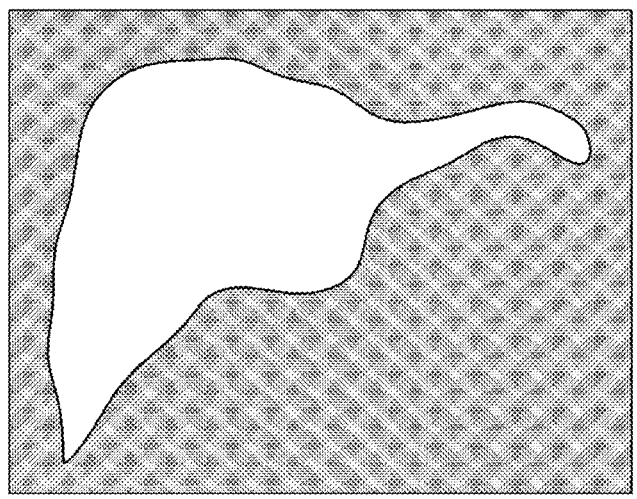
(b) EXHALATION
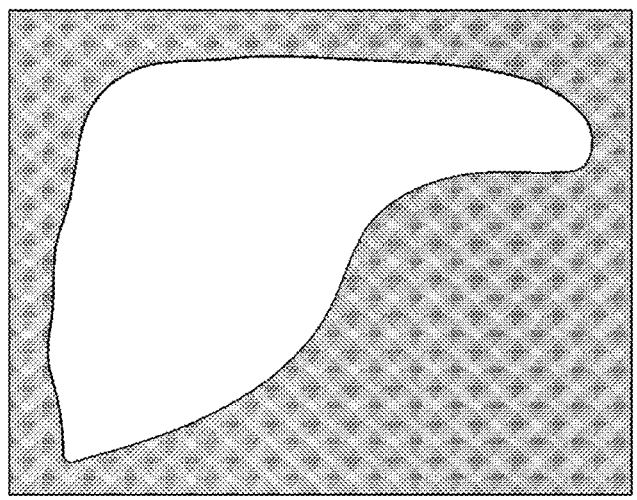

FIG. 11
(a) INHALATION
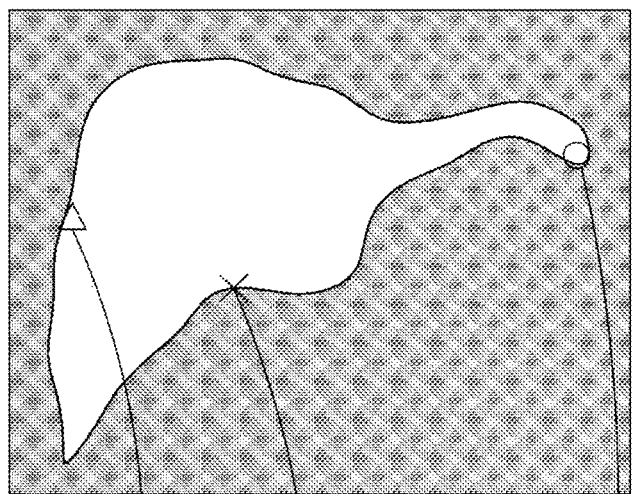
(b) EXHALATION
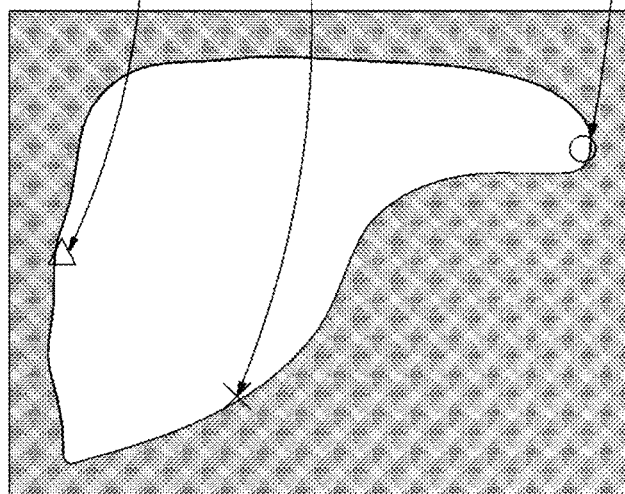

FIG. 12
(a) INHALATION : MR
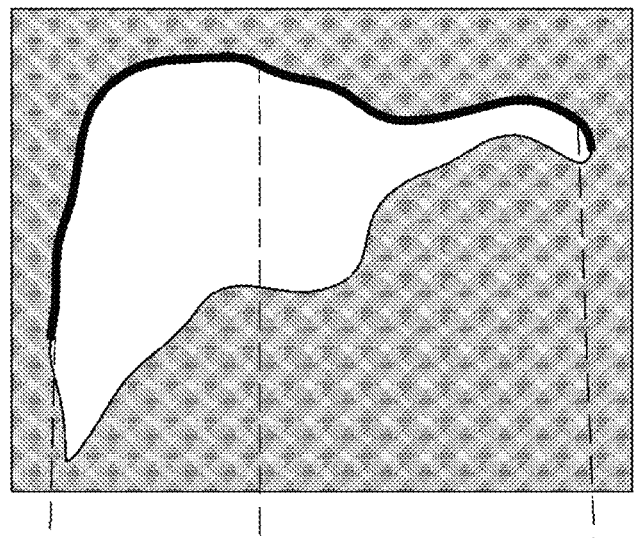
(b) INHALATION : CT
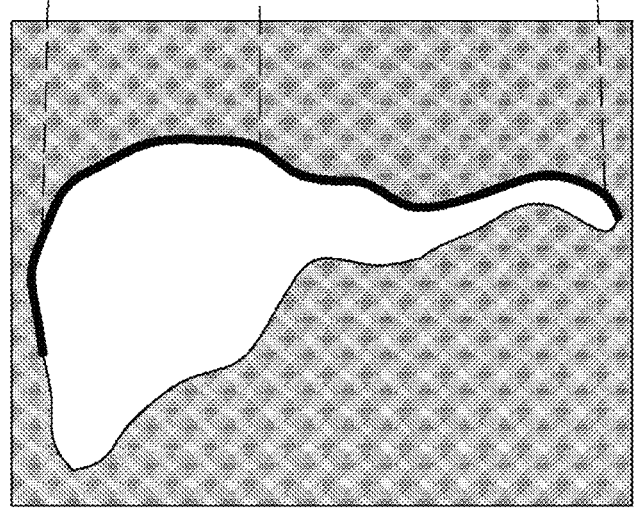

FIG. 13
(a) INHALATION
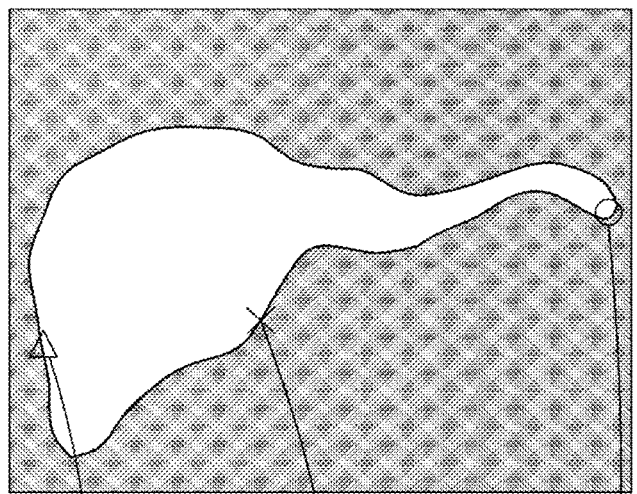
(b) EXHALATION
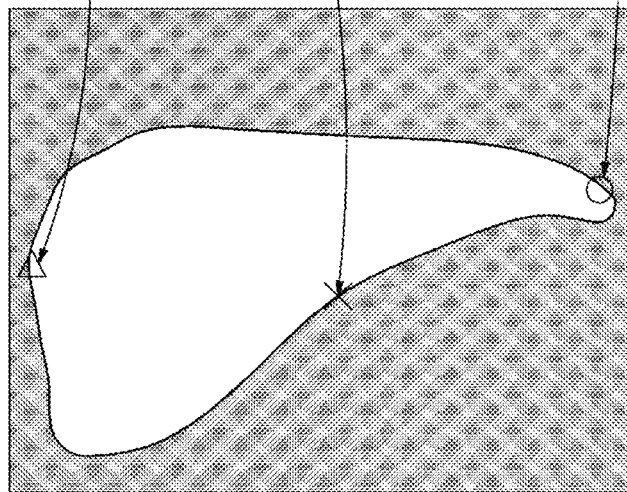

FIG. 14
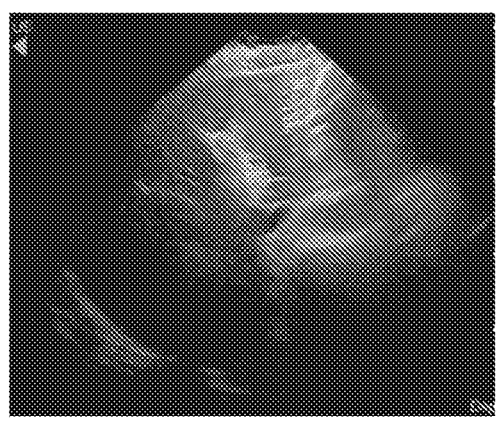
(a)
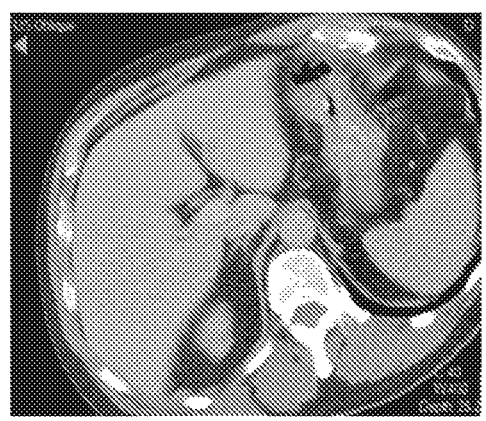
(b)
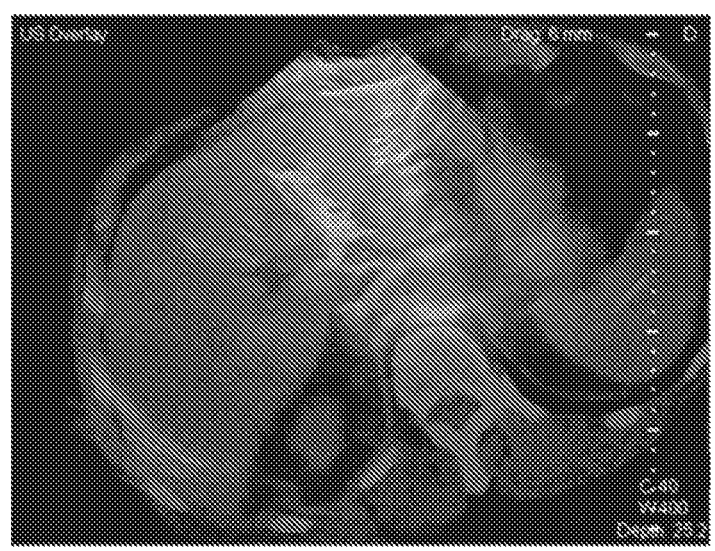
(c)

IMAGE PROCESSING APPARATUS, IMAGE PROCESSING METHOD, AND ULTRASOUND IMAGING APPARATUS HAVING IMAGE PROCESSING UNIT

CROSS-REFERENCE TO RELATED APPLICATION

This application claims the benefit of Korean Patent Application No. 10-2014-0148242, filed on Oct. 29, 2014 in the Korean Intellectual Property Office, the disclosure of which is incorporated herein by reference.

BACKGROUND

1. Field

Exemplary embodiments relate to an image processing apparatus, an image processing method, and an ultrasound imaging apparatus having an image processing unit, and relate to an apparatus and method for registering medical images having different modalities.

2. Description of the Related Art

Computed Tomography (CT) is a type of medical imaging apparatus that has a high signal to noise ratio and a high resolution and is able to relatively clearly observe a very small object. Also, since a CT system may provide a cross-sectional image of an object, an internal structure (for example, organs such as a kidney, a liver, and a lung) of the object may be displayed without being overlapped by other images, unlike general X-ray imaging apparatuses, and almost all diseases such as brain disease, lung cancer, esophageal cancer, liver cancer, gastrointestinal tumor, and bone tumor may be examined. However, since CT carries a risk of radiation exposure according to use of ionizing radiation X-rays, imaging should be performed only when absolutely required.

Compared to other diagnostic apparatuses such as a CT system or a magnetic resonance imaging (MRI) system, an ultrasound (US) apparatus has a low signal to noise ratio, has relatively unclear image quality, and cannot easily be used to examine diseases such as cancer and tumor, but has almost no side effects on a body and is able to obtain an image in real time. Therefore, the US apparatus has been widely used in medical fields that require information on a patient's internal areas in real time such as lesion diagnosis, biopsy, and radio-frequency ablation.

SUMMARY

As a method of complementing drawbacks of CT and ultrasound (US) imaging systems, exemplary embodiments provide an image processing apparatus, an image processing method, and an ultrasound imaging apparatus having an image processing apparatus in which a US image obtained in a real time procedure using a US and a cross section of a CT image corresponding thereto are found and registered and then the images are fused and displayed.

Specifically, deformation of an organ occurs according to a difference between a CT image and an US image caused by a difference of respiration phases, and image quality of a fusion image decreases due to the resulting registration error. In order to prevent such problems, there are provided an image processing apparatus, an image processing method, and an ultrasound imaging apparatus having an image processing apparatus in which a US image and a CT image of the same respiration phase are fused and used using a magnetic resonance (MR) image database including inspiration and expiration phases of a plurality of patients.

According to an aspect of an exemplary embodiment, there is provided an image processing apparatus, including an input device configured to receive a computerized tomography image of a first respiration phase of an object; a data selector configured to select magnetic resonance image data similar to the object from among magnetic resonance image data; and an image generator configured to generate a computerized tomography image of a second respiration phase of the object based on the selected magnetic resonance image data.

The data selector may include a similarity determiner configured to determine similarity of anatomical features between the object and the magnetic resonance image data and to select the magnetic resonance image data based on the determined similarity, and wherein the anatomical features may include a shape and a size of the object.

The computerized tomography image of the first respiration phase may be a computerized tomography image of the object during inhalation, and the computerized tomography image of the second respiration phase may include a computerized tomography image of the object during exhalation.

The image processing apparatus may further include a storage configured to store 4D magnetic resonance image data of the object.

The image processing apparatus may further include an image extractor configured to extract a magnetic resonance image of the first respiration phase and a magnetic resonance image of the second respiration phase based on the magnetic resonance image data similar to the object.

The image processing apparatus may further include a displacement vector generator configured to determine a movement displacement vector of the object based on the extracted magnetic resonance image of the first respiration phase and the extracted magnetic resonance image of the second respiration phase.

The image processing apparatus may further include a first image registrator configured to register the extracted magnetic resonance image of the first respiration phase to the computerized tomography image of the first respiration phase of the object.

The image generator may include a displacement vector applier configured to apply the determined movement displacement vector of the object to the computerized tomography image of the first respiration phase of the object.

The image processing apparatus may include a second image registrator configured to register a computerized tomography image of the object to an ultrasound image of the object based on the computerized tomography image of the first respiration phase of the object and the generated computerized tomography image of the second respiration phase of the object.

According to another aspect of an exemplary embodiments, there is provided an image processing method, including receiving a computerized tomography image of a first respiration phase of an object; selecting magnetic resonance image data similar to the object from among magnetic resonance image data; and generating a computerized tomography image of a second respiration phase of the object based on the selected magnetic resonance image data.

The selecting of the magnetic resonance image data similar to the object may include determining a similarity between anatomical features of the object and the magnetic resonance image data and selecting the magnetic resonance image data based on the determined similarity.

The computerized tomography image of the first respiration phase may be a computerized tomography image of the object during inhalation, and the computerized tomography image of the second respiration phase may include a computerized tomography image of the object during exhalation.

The image processing method may further include extracting a magnetic resonance image of the first respiration phase and a magnetic resonance image of the second respiration phase based on the magnetic resonance image data similar to the object.

The image processing method may further include determining a movement displacement vector of the object based on the extracted magnetic resonance image of the first respiration phase and the extracted magnetic resonance image of the second respiration phase.

The image processing method may include registering the extracted magnetic resonance image of the first respiration phase to the computerized tomography image of the first respiration phase of the object.

The generating of the computerized tomography image of the second respiration phase of the object may include applying the determined movement displacement vector of the object to the computerized tomography image of the first respiration phase of the object.

The image processing method may further include registering a computerized tomography image of the object to an ultrasound image of the object based on the computerized tomography image of the first respiration phase of the object and the generated computerized tomography image of the second respiration phase of the object.

According to still another aspect of an exemplary embodiment, there is provided an ultrasound imaging apparatus including an ultrasound probe configured to obtain an ultrasound image signal of an object; a communicator configured to receive a computerized tomography image of a first respiration phase of the object and magnetic resonance image data similar to the object; and an image processor configured to generate a computerized tomography image of a second respiration phase of the object and register a computerized tomography image of the object to the ultrasound image of the object based on the computerized tomography image of the first respiration phase of the object, the computerized tomography image of the second respiration phase of the object, and the magnetic resonance image data similar to the object.

The ultrasound imaging apparatus may further include a display configured to display the registered computerized tomography image of the object and the ultrasound image of the object.

The ultrasound imaging apparatus may further include a storage configured to store the received computerized tomography image of the first respiration phase of the object and the magnetic resonance image data similar to the object.

BRIEF DESCRIPTION OF THE DRAWINGS

These and/or other aspects of the exemplary embodiments will become apparent and more readily appreciated from the following description of the exemplary embodiments, taken in conjunction with the accompanying drawings of which:

FIG. 5 shows magnetic resonance images of a liver of a normal person and liver cancer;

FIG. 6 shows shapes of a liver according to a respiration phase;

FIG. 11 shows movement of coordinates for calculating a movement displacement vector in a first respiration phase and a second respiration phase of the liver;

FIG. 12 shows a concept of registration of a computerized tomography image of a first respiration phase and a magnetic resonance image of the first respiration phase of the liver according to an exemplary embodiment;

FIG. 13 shows generation of a computerized tomography image of a second respiration phase of the liver by applying a displacement vector determined from magnetic resonance image data of the liver to computerized tomography image data of a first respiration phase;

FIG. 14 shows an image that is obtained by registering a computerized tomography image to an ultrasound image according to an exemplary embodiment.

DETAILED DESCRIPTION

Figure 1:
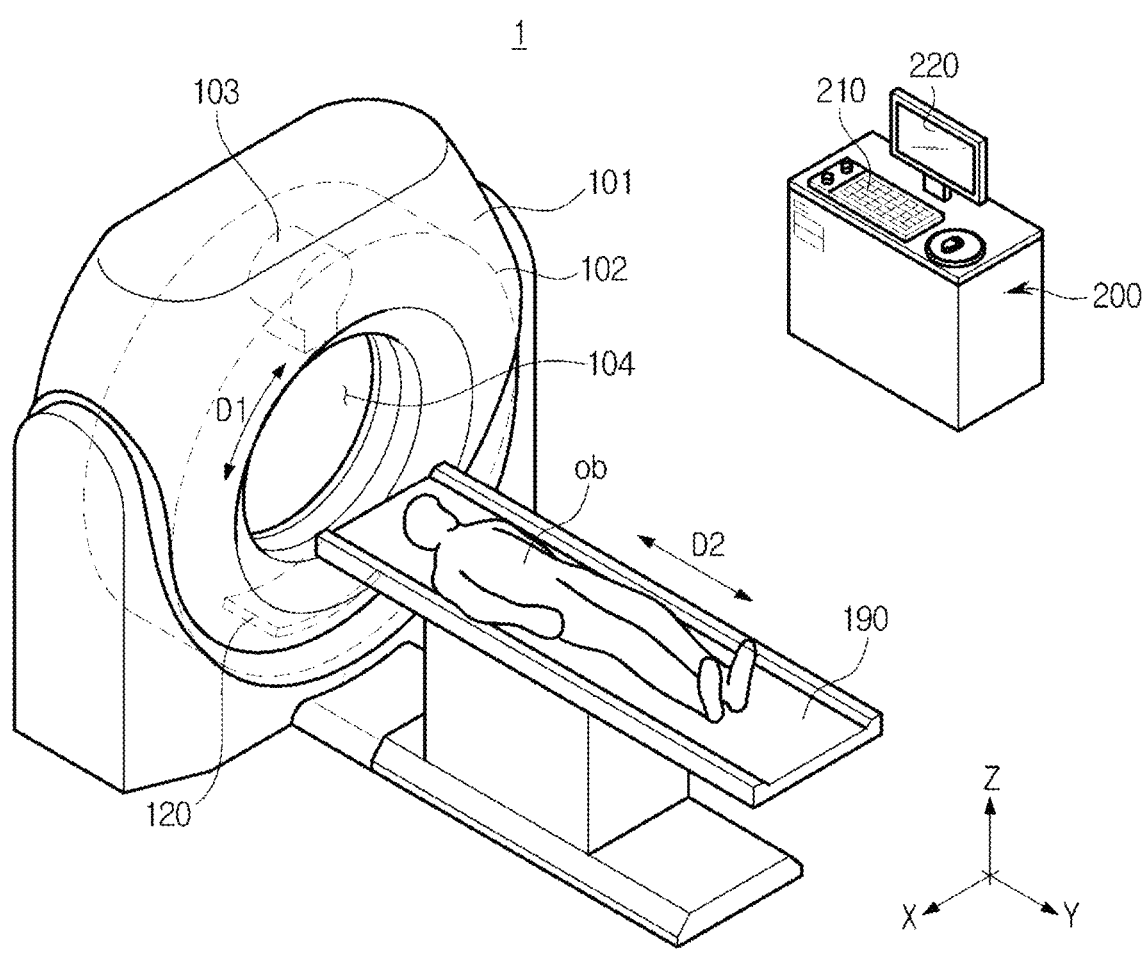
FIG. 1 is a perspective view of an X-ray imaging apparatus implemented as a computerized tomography apparatus according to an exemplary embodiment.

Advantages and features of the exemplary embodiments, and methods of achieving the same will be clearly understood with reference to the accompanying drawings and the following detailed exemplary embodiments.

Exemplary embodiments described in this specification and configurations illustrated in drawings are only exemplary examples. It is understood that the exemplary embodiments cover various modifications that can substitute the exemplary embodiments herein and drawings at the time of filing of this application.

Hereinafter, an ultrasound imaging apparatus and a method of controlling the same according to exemplary embodiments will be described with reference to the accompanying drawings. Like reference numerals refer to like elements throughout.

As described above, computerized tomography (CT) is a type of medical imaging apparatus that has an image of a high signal to noise ratio and a high resolution, is able to relatively clearly observe a very small object and identify lesions such as cancer or tumor. However, since there is a risk of radiation exposure according to use of X-rays, imaging should be performed as little as possible. Compared to the CT image, an ultrasound image has a lower signal to noise ratio than those of other diagnostic apparatuses such as CT and MRI, has low image quality, and is difficult to identify lesions such as cancer or tumor, but has almost no side effects on a body and is able to obtain an image in real time. Therefore, an ultrasound (US) image has been widely used in medical fields that require information on a patient's internal areas in real time such as lesion diagnosis, biopsy, and radio-frequency ablation.

In general, when computerized tomography is performed on a patient's object, the patient takes a deep breath (inspiration) to image. On the other hand, the US imaging is performed in a relaxed respiration state (rest). In the object such as organs in the abdomen, due to a difference of such a respiration phase, organ deformation occurs. Accordingly, when a computerized tomography image and an ultrasound image are registered in order to observe the images at the same coordinates or position at the same time, registration errors may be caused, image quality of the registered image may be deteriorated, and it may be difficult to observe the images at the same coordinates or position at the same time.

In order to address such problems, in the related art, a registration method in which a professional manually extracts common features from a computerized tomography image and an ultrasound image of an object, and then uses a technique in which a specifically designed energy function is minimized based on correspondence of features, has been used. However, this method is inefficient and inconvenient since much time and expertise are required when a process of manually extracting common features is applied to a 3D medical image.

As another method, a method in which a simulation is performed on a computerized tomography image to fuse a virtual 3D ultrasound image, and then non-rigid registration of maximizing a correlation ratio between an ultrasound image obtained in real time and a virtual 3D ultrasound image is derived, has been used. Since a simulation conversion model varies for each object such as organs of a body and many conversion functions are nonlinear, it is very difficult to find an appropriate coefficient. Therefore, when this method is applied to an actual image, performance may be worse than expected, which results in many problems.

As still another method, a method in which a professional separates and segments blood vessels and organs of a computerized tomography image in advance, rigid registration is performed based on a blood vessel centerline, and non-rigid registration of minimizing entropy at a boundary area of the organ is additionally found, has been used. However, according to this method, it is sometimes difficult to separate an appropriate blood vessel in an ultrasound image according to a state of an object such as a patient's organ, and performing an algorithm may take several hours, and therefore an application to an actual product is inappropriate for use.

Therefore, in an image processing apparatus, an image processing method, and an ultrasound imaging apparatus having an image processing apparatus according to an exemplary embodiment, it is proposed to fuse and use an ultrasound image and a computerized tomography image of the same respiration phase in order to reduce a registration error caused by a difference of respiration phases when the computerized tomography image and the ultrasound image are registered.

A medical image generating apparatus to which technology of the image processing apparatus, the image processing method, and the ultrasound imaging apparatus having an image processing apparatus according to an exemplary embodiment may be applied or used may refer to any of an X-ray imaging apparatus, an X-ray fluoroscopic apparatus, a CT scanner, a magnetic resonance imaging (MRI) apparatus, a positron emission tomography (PET) apparatus, and an ultrasound imaging apparatus. While the present exemplary embodiments exemplify the CT apparatus and the ultrasound imaging apparatus, the exemplary embodiments are not limited thereto. Hereinafter, the term "ultrasound image" refers to an image of an object that is obtained using an ultrasound, the term "computerized tomography image" refers to an image of an object that is obtained using CT, and the term "magnetic resonance image" refers to an image of an object that is obtained using the MRI apparatus. Also, the term "object" may refer to a human, a fetus, an animal, a metal, a nonmetal, or a part thereof. The object may include, for example, an organ such as a liver, a kidney, a lung, a heart, a uterus, a brain, a breast, or an abdomen, or a blood vessel. In addition, the object may include a phantom, and the phantom may refer to a material that has a density of an organism and a volume that is very close to an effective atomic number.

For convenience of description, while exemplary embodiments to be described below exemplify a case in which the object is the "liver," the exemplary embodiments are not limited thereto.

Also, the term "user" used hereinbelow may be a medical professional such as a doctor, a nurse, a clinical pathologist, a medical image professional, an ultrasound examiner, or a technician who repairs a medical apparatus, but the exemplary embodiments are not limited thereto.

FIG. 1 is a perspective view of an X-ray imaging apparatus implemented as a computerized tomography apparatus according to an exemplary embodiment.

As illustrated in FIG. 1, an X-ray imaging apparatus 1 may include a housing 101 configured to radiate and detect X-rays, a table 190 configured to move an object (ob), and a main body 200 configured to control an operation of the X-ray imaging apparatus 1.

A cylindrical gantry 102 is mounted in the housing 101. In the gantry 102, an X-ray source 103 configured to radiate X-rays and an X-ray detector 120 configured to detect X-rays are provided to face each other. The X-ray source 103 is an apparatus that generates X-rays and radiates the X-rays to the object, and may be provided in the form of an X-ray source assembly including a filtering unit configured to filter radiated X-rays and the like. Here, the object may include any object of which an internal structure can be imaged by the X-ray imaging apparatus 1 such as a human, an animal, and goods.

The X-ray detector 120 is an apparatus that detects X-rays transmitted through the object and may be provided in a position opposite to the X-ray source 103. According to movement of the table 190, the object may be positioned between the X-ray source 103 and the X-ray detector 120, and X-rays radiated from the X-ray source 103 may transmit through the object and be detected by the X-ray detector 120.

According to a driving command, the gantry 102 rotates around a bore 104 at a constant angular velocity. Therefore, the X-ray source 103 and the X-ray detector 120 provided in the gantry 102 also form a predetermined axis and rotate. In this case, a direction in which the gantry 102 rotates may be defined as a direction D1.

The table 190 transfers an object serving as a target of X-ray imaging into the bore 104. The table 190 maintains a horizontal state with respect to the ground and may move in a horizontal direction (that is, an x axis direction), a vertical direction (that is, a y axis direction) and an anteroposterior direction (that is, a z axis direction). While moving in the x axis direction, y axis direction, and z axis direction, the table 190 allows an area to be imaged, that is, a field of view (FOV) to be positioned between the X-ray source 103 and the X-ray detector 120. In this case, a direction in which the table 190 moves in the y axis direction may be defined as a direction D2. Also, the FOV may include an entire object or only a partial area inside the object. The FOV may also be a region of interest (ROI).

The main body 200 may accommodate a main component of the X-ray imaging apparatus 1, for example, a control unit (not illustrated). The control unit may generate various control signals for operations of the X-ray imaging apparatus 1 in order to control rotation of the gantry 102, movement of the table 190, or an X-ray dose radiated from the X-ray source 103.

A user interface for user manipulation may be provided above the main body 200. The user interface may include an input unit 210 configured to receive a user command for manipulating operations of the X-ray imaging apparatus 1 and a display unit 220 configured to provide various screens related to operations of the X-ray imaging apparatus 1.

The input unit 210 may include a hardware input device to receive user input such as various buttons, a switch, a keyboard, a mouse, a trackball, various levers, a handle, or a stick. The input unit 210 may be provided above the main body 200 as illustrated in FIG. 1, but may be provided below the main body 200 when the input unit 210 is implemented as a foot switch or a foot pedal.

The input unit 210 may include a graphical user interface (GUI) such as a touch pad for a user input, that is, a software input device. The touch pad may be implemented as a touch screen panel (TSP).

The user may input an X-ray imaging start command, a moving command of the table 190, and the like through the input unit 210, select a type of imaging or set the FOV, or the like. The user command input to the input unit 210 may be transmitted to the main body 200 via wired communication or wireless communication.

The display unit 220 may include a cathode ray tube (CRT), a digital light processing (DLP) panel, a plasma display panel, a liquid crystal display (LCD) panel, an electro luminescence (EL) panel, an electrophoretic display (EPD) panel, an electrochromic display (ECD) panel, a light emitting diode (LED) panel, an organic light emitting diode (OLED) panel, or the like, but the exemplary embodiments are not limited thereto.

As described above, when a touch screen panel (TSP) forming a cross-layer structure with a touch pad is provided, the display unit 220 may be used as an input device in addition to a display device.

The display unit 220 may display screens related to operation information of the X-ray imaging apparatus 1 such as a screen for selecting a type of imaging and a screen for setting FOV, and display X-ray images obtained through X-ray imaging. Here, the X-ray images may include a reconstructed image close to an ideal image inside the object and an image obtained by performing post-processing on the reconstructed image.

According to a type of imaging, the X-ray image obtained through X-ray imaging may be a single cross-sectional image, a plurality of cross-sectional images, or a 3D image or a 3D stereo image generated based on a plurality of cross-sectional images. In this case, the 3D image refers to an image that is obtained by performing volume rendering of 3D volume data generated based on a plurality of cross-sectional images based on a predetermined time. That is, the 3D image refers to a 2D projected image that is obtained by projecting volume data onto a 2D plane based on a predetermined time. The 3D stereo image refers to an image in which volume rendering of volume data at two viewpoints corresponding to the user's left and right eyes, respectively, is performed to obtain a left image and a right image and the two obtained images are combined.

Unlike the case illustrated in FIG. 1, the display unit 220 may include a plurality of display devices and display different types of screens. As an example, the display unit 220 may include a first display device and a second display device. The first display device may display the cross-sectional image and the second display device may display the 3D image or the 3D stereo image. As another example, the first display device may display a screen related to operation information of the X-ray imaging apparatus 1, and the second display device may display X-ray images obtained through X-ray imaging.

A CT image of the object may be obtained using the above computerized tomography apparatus.

Figure 2:
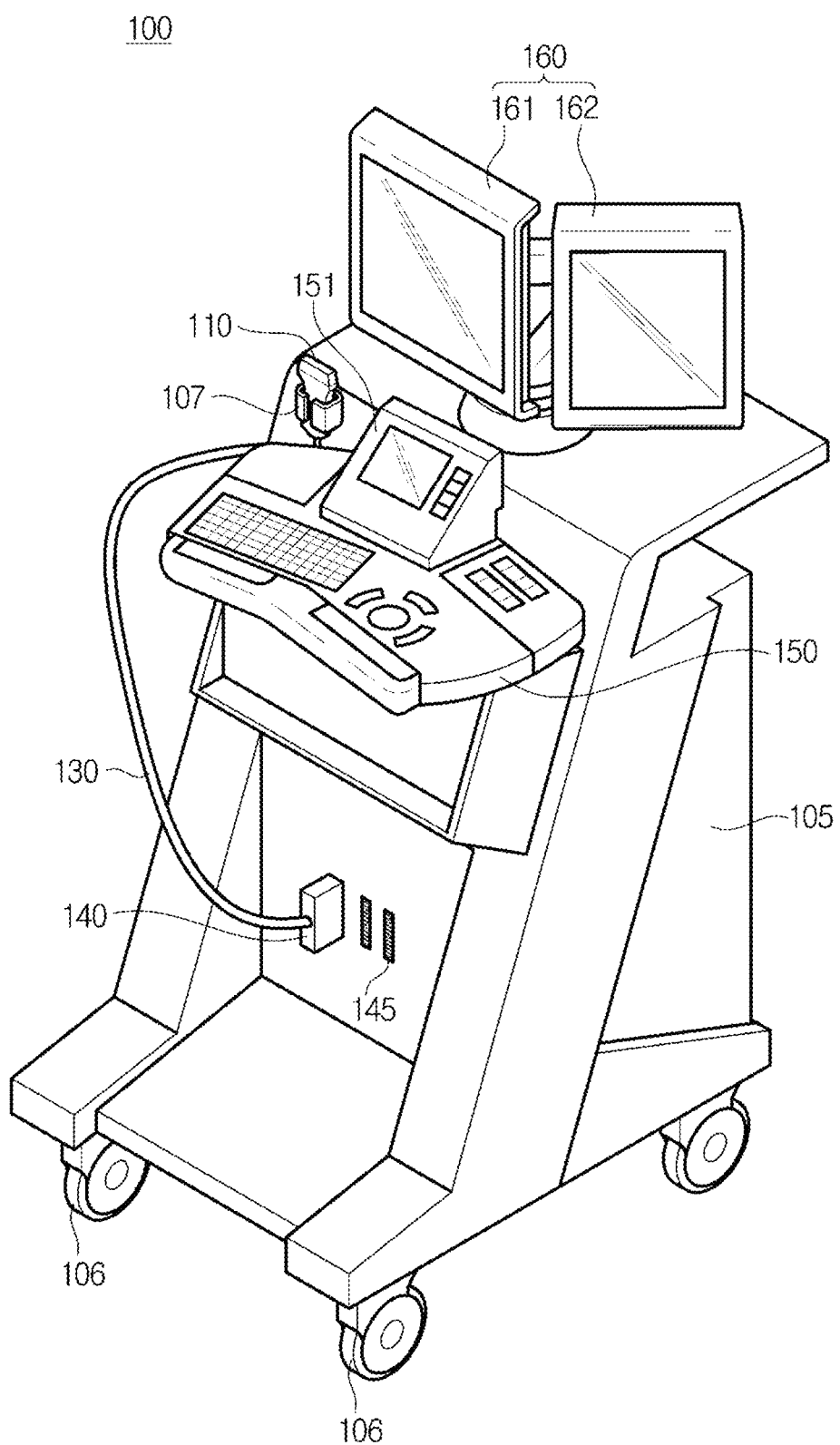
FIG. 2 is a perspective view of an ultrasound imaging apparatus according to an exemplary embodiment.

FIG. 2 is a perspective view of an ultrasound imaging apparatus according to an exemplary embodiment.

As illustrated in FIG. 2, an ultrasound imaging apparatus 100 may include a probe 110, a main body 105, a manipulation panel 150, and a display unit 160 (e.g., "display").

At least one female connector 145 may be provided in the front lower side of the main body 105. A male connector 140 provided in one end of a cable 130 may be physically coupled to the female connector 145. The ultrasound probe 110 and the main body 105 may be connected through the cable 130.

Meanwhile, a plurality of casters 106 for moving the ultrasound apparatus may be provided below the main body 105. The user may fix the ultrasound imaging apparatus 100 at a specific place or move the ultrasound imaging apparatus 100 in a specific direction using the plurality of casters 106. This ultrasound imaging apparatus 100 is referred to as a cart type ultrasound apparatus.

Meanwhile, unlike the case in FIG. 2, the ultrasound imaging apparatus 100 may be a mobile ultrasound apparatus that may be carried when moving in a long distance. In this case, the mobile ultrasound apparatus may not include the casters 106. Examples of the mobile ultrasound imaging apparatus 100 may include a PACS viewer, a smartphone, a laptop computer, a PDA, and a tablet PC, but the exemplary embodiments are not limited thereto.

The ultrasound probe 110 is a unit that comes in contact with a body surface of the object and may transmit and receive an ultrasound to and from the object. Specifically, the ultrasound probe 110 generates an ultrasound according to an input pulse, transmits the ultrasound into the object, and receives an echo ultrasound reflected from a specific area inside the object.

The manipulation panel 150 is a unit capable of receiving a command related to an operation of the ultrasound imaging apparatus 100. The user may input a command for performing a diagnosis start, a diagnosis area selection, a diagnosis type selection, or a mode selection of an ultrasound image to be finally output through the manipulation panel 150. Exemplary modes of the ultrasound image may include an amplitude mode (A-mode), a brightness mode (B-mode), a Doppler mode (D-mode), an elastography mode (E-mode), and a motion mode (M-mode).

According to an exemplary embodiment, as illustrated in FIG. 2, the manipulation panel 150 may be positioned above the main body 105. In this case, the manipulation panel 150 may include at least one of a switch, a key, a wheel, a joystick, a trackball, and a knob.

Also, the manipulation panel 150 may further include a sub display 151. The sub display 151 may be provided in one side of the manipulation panel 150 and display information about manipulation of the ultrasound imaging apparatus 100.

For example, the sub display 151 may display a menu, an instruction, and the like for setting the ultrasound imaging apparatus 100, or display current settings of the ultrasound imaging apparatus 100.

In this case, the sub display 151 may be implemented as a touch panel. When the sub display 151 is implemented as the touch panel, the user may touch the sub display 151 and input a control command.

The sub display 151 may be implemented as, for example, a liquid crystal display (LCD) panel, a light emitting diode (LED) panel, an organic light emitting diode (OLED) panel, or the like.

At least one holder 107 of the probe 110 for mounting the ultrasound probe 110 may be provided in the vicinity of the manipulation panel 150. Therefore, when the ultrasound imaging apparatus 100 is not used, the user may mount and keep the ultrasound probe 110 on the holder 107 of the probe 110.

The display unit 160 may display ultrasound images obtained in a process of ultrasound diagnosis. As illustrated in FIG. 2, the display unit 160 may be coupled to and mounted on the main body 105, or may be implemented to be detachable from the main body 105.

Also, the display unit 160 may include a plurality of display devices 161 and 162 and display different images at the same time. For example, the first display device 161 may display an ultrasound image that is obtained by imaging the object, and the second display device 162 may display a registration image. The first display device 161 may display a 2D image that is obtained by imaging the object, and the second display device 162 may display a 3D image.

Also, each of the display devices 161 and 162 may include a display panel such as a plasma display panel (PDP), a liquid crystal display (LCD) panel, a light emitting diode (LED) panel, an organic light emitting diode (OLED) panel, or an active-matrix organic light-emitting diode (AMOLED) panel.

It is possible to obtain an ultrasound image of the object using the above ultrasound imaging apparatus.

Figure 3:
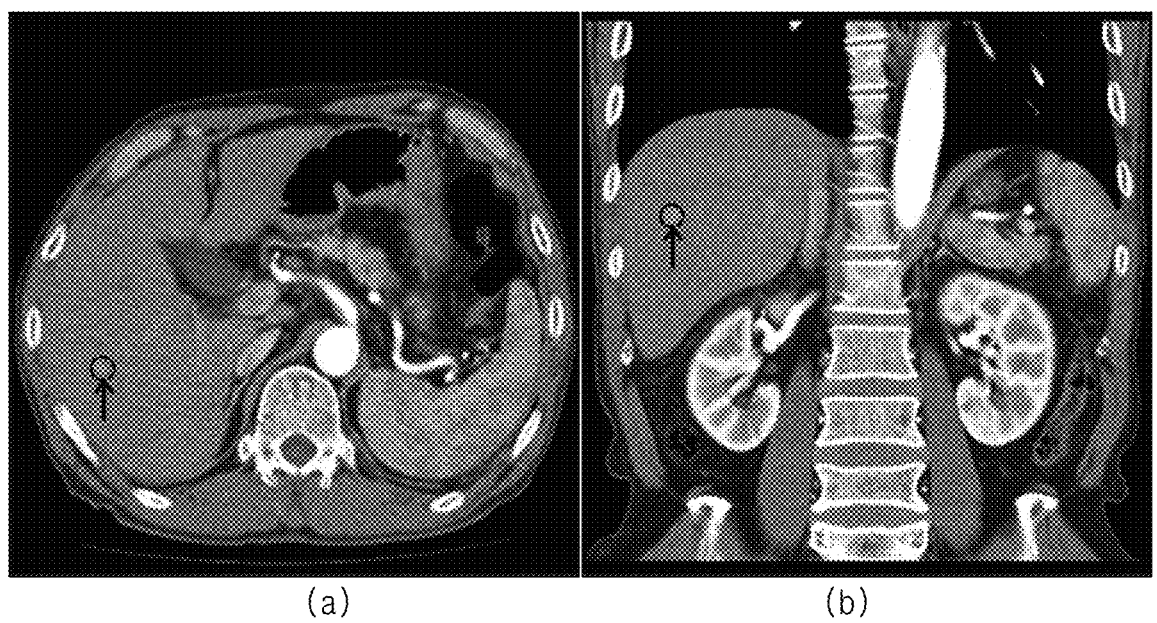
FIG. 3 shows pictures of computerized tomography (CT) images of liver cancer.

FIG. 3 shows pictures of computerized tomography (CT) images of liver cancer.

FIG. 3 shows pictures of computerized tomography images of a patient's abdomen. (b) of FIG. 3 shows a general computerized tomography image of an abdomen area. (a) of FIG. 3 shows an image of a liver area serving as an object.

As shown in (a) of FIG. 3, a gray area left on the screen corresponds to a liver area, and an area that is indicated by an arrow and is more slightly white than surroundings corresponds to liver cancer. That is, according to an actual measurement value, it is a tumor of about 1.3 cm and diagnosed as early liver cancer. In this manner, through the computerized tomography image, it is possible to diagnose liver cancer of a tumor area. Since the computerized tomography image has a higher resolution than an ultrasound image to be described, it is possible to relatively clearly observe a cancer area.

Figure 4:
FIG. 4 shows an ultrasound image of liver cancer.

FIG. 4 shows an ultrasound image of liver cancer.

As illustrated in FIG. 4, an area indicated by an arrow corresponds to a tumor of a size of 1.3 cm that is suspected as liver cancer. As shown in the image of FIG. 4, the ultrasound image is able to be obtained and displayed in real time, but has a lower signal to noise ratio and lower image quality than the computerized tomography image in FIG. 3. Accordingly, it is difficult to identify an area displayed as liver cancer. Therefore, since early detection of liver cancer and the like is difficult using only ultrasound image examination, an examination of computerized tomography or magnetic resonance imaging is accompanied for accurate diagnosis.

FIG. 5 shows magnetic resonance images of a liver of a normal person and liver cancer.

As shown in FIG. 5, (a) of FIG. 5 shows a magnetic resonance image (MRI) of a normal person's liver, and (b) of Figure shows an early liver cancer area that is determined in the magnetic resonance image. As shown in (a) of FIG. 5, it can be understood that the magnetic resonance image includes the liver area that is relatively clearly displayed and has a higher resolution than the ultrasound image shown in FIG. 4, and therefore the liver serving as an object may be clearly observed. Also, as shown in (b) of FIG. 5, areas indicated by an arrow in the left image and the right image correspond to early liver cancer areas and represent early liver cancer areas of a size of 1.3 cm and 5 mm, respectively. The cancer area is more clearly identified in the magnetic resonance image than the ultrasound image or the computerized tomography image. It can be understood that the cancer area of 1.3 cm on the left is identified in the computerized tomography image, but the cancer area of 5 mm on the right is not identified in the computerized tomography image but may be identified in the magnetic resonance image.

FIG. 6 shows shapes of a liver according to a respiration phase.

As illustrated in FIG. 6, (a) of FIG. 6 illustrates a shape of the liver during inspiration, that is, during inhalation, and (b) of FIG. 6 illustrates a shape of the liver during expiration, that is, during exhalation. The liver is positioned below a diaphragm that is an upper right area of the abdomen and protected by surrounding ribs. As illustrated in (a) of FIG. 6, when the user inhales, the lung expands and the diaphragm moves down. Therefore, compared to expiration, the liver is relatively pressed and has a flat shape. On the other hand, as illustrated in (b) of FIG. 6, when the user exhales, the lung contracts and the diaphragm moves up. Therefore, compared to inspiration, the liver has a relatively expanded shape.

From a relative position of the liver according to such respiration, it is possible to calculate a movement displacement vector about a direction and an amount of change of reference points of the liver. Descriptions thereof will be provided below in the section of movement displacement vector determination.

Figure 7:
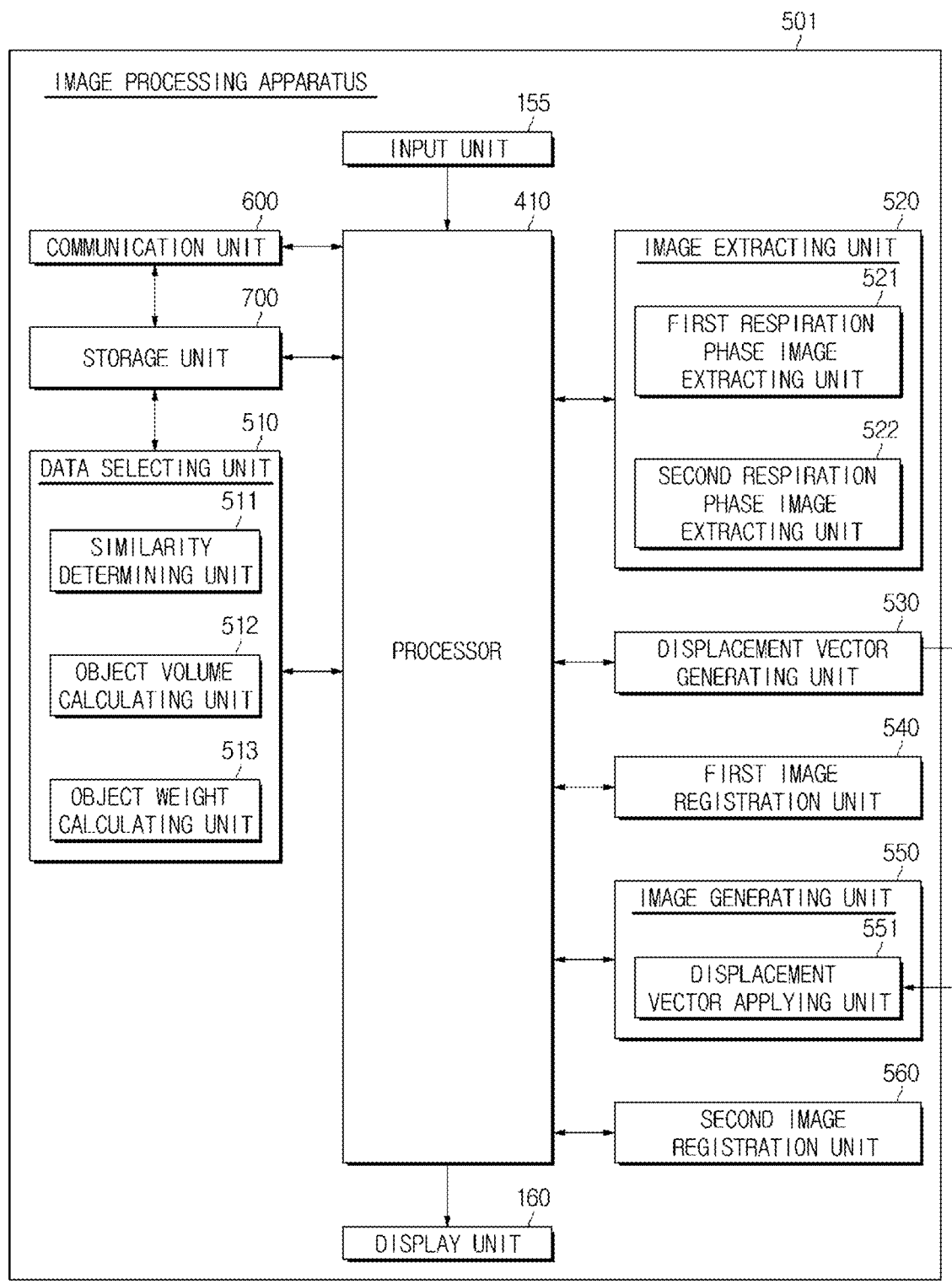
FIG. 7 is a control block diagram of an image processing apparatus according to an exemplary embodiment.

FIG. 7 is a control block diagram of an image processing apparatus according to an exemplary embodiment.

The image processing apparatus according to an exemplary embodiment may be executed in the medical diagnostic apparatus or the medical image generating apparatus such as the ultrasound imaging apparatus, and may also be operated as a separate image processing apparatus according to software control.

As illustrated in FIG. 7, an image processing apparatus 501 may include a processor 410, a data selecting unit 510 (e.g., data selector), an image extracting unit 520 (e.g., image extractor), a displacement vector generating unit 530 (e.g., displacement vector generator), a first image registration unit 540 (e.g., first image registrator), an image generating unit 550 (e.g., image generator), a second image registration unit 560 (e.g., second image registrator), a communication unit 600 (e.g., communicator), a storage unit 700 (e.g., storage), an input unit 155 (e.g., input device) and the display unit 160 (e.g., display). The data selecting unit 510 may include a similarity determining unit 511 (e.g., similarity determiner), an object volume calculating unit 512 (e.g., object volume calculator), and an object weight calculating unit 513 (e.g., object weight calculator). Also, the image extracting unit 520 may include a first respiration phase image extracting unit 521 (e.g., first respiration phase image extractor) and a second respiration phase image extracting unit 522 (e.g., second respiration phase image extractor). The image generating unit 550 may include a displacement vector applying unit 551 (e.g., displacement vector applier).

A first respiration phase refers to an inspiration state (inhalation). A second respiration phase refers to an expiration state (exhalation).

The processor 410 controls components of the image processing apparatus 501. Each of the components performs a function through an interaction with the processor 410.

The input unit 155 inputs data related to an exemplary embodiment to the image processing apparatus 501. Data of the computerized tomography image of the liver serving as an object may be input through the input unit 155. Since the computerized tomography image is imaged in an inspiration state in which the user has taken a deep breath, the user may input the computerized tomography image of the liver during inspiration. Also, through the input unit 155, magnetic resonance image data of the liver serving as an object may also be input. Since magnetic resonance image data of the liver is different for each person and types of information are various, data of the object obtained from a magnetic resonance imaging apparatus may be input and used to obtain data of the object having information similar to that of a target patient. Also, information on the patient's body including the object may be input through the input unit 155, and the information on the patient's body may specifically include the patient's anatomical features such as a gender, an age, a body height, a body weight, and a waistline, and may also include information on severity of disease. The information on the object input through the input unit 155 is used as an indicator of similarity determination for selecting magnetic resonance image data of the object stored in the storage unit 700. In addition to the above-described content, data to be used to implement the technique of the exemplary embodiment may be input.

The communication unit 600 may be connected to other apparatuses and transmit and receive data to and from the connected apparatus. In particular, the communication unit 600 may receive image data of the liver serving as an object that is imaged by the computerized tomography apparatus, receive a patient's body information or anatomical features input to other apparatuses, and receive magnetic resonance image data of the liver that is imaged by the magnetic resonance imaging apparatus. As described above, data may be directly input through the input unit 155, and data received by the communication unit 600 may be used. The communication unit 600 may transmit the received data to the processor 410, store the data in the storage unit 700, and use the data for first image registration and second image registration according to an exemplary embodiment.

Here, another apparatus images the object using a preset method and obtains a medical image. The other apparatus may be an apparatus that has a different modality from the ultrasound imaging apparatus 100. For example, the other apparatus may be one of a magnetic resonance imaging (MRI) apparatus, a computerized tomography (CT) apparatus, a positron emission tomography (PET) apparatus, and a single photon emission computed tomography (SPECT) apparatus.

The communication unit 600 may perform data communication with the other apparatus according to various wired and/or wireless communication protocols, and may perform data communication according to a digital imaging and communications in medicine (DICOM) standard.

The storage unit 700 may store data to be used for image registration according to an exemplary embodiment. Computerized tomography image data and magnetic resonance image data of the liver serving as an object may be stored. As described above, the image data may be directly input through the input unit 155 and may be received from the other apparatus through the communication unit 600. The data stored in the storage unit 700 is transmitted to the processor 410, the data selecting unit 510, the image extracting unit 520, the displacement vector generating unit 530, the first image registration unit 540, the image generating unit 550, and the second image registration unit 560, and may be used for image generation and image registration.

The data selecting unit 510 may include the similarity determining unit 511, the object volume calculating unit 512, and the object weight calculating unit 513, and may select magnetic resonance image data of a liver having a condition similar to the liver from computerized tomography image data of the first respiration phase of the liver serving as an object.

The similarity determining unit 511 may perform similarity determination based on anatomical feature information of the object input through the input unit 155 or received through the communication unit 600. Criteria of similarity determination may include a volume, a weight, and the like of the liver and may be calculated by the object volume calculating unit 512 and the object weight calculating unit 513 based on information on the patient's body including the object. Similarity is determined by comparing the volume, weight, and the like.

The image extracting unit 520 may include the first respiration phase image extracting unit 521 and the second respiration phase image extracting unit 522. Based on magnetic resonance image data similar to the input computerized tomography image data of the object, a magnetic resonance image of the first respiration phase and a magnetic resonance image of the second respiration phase may be extracted.

The displacement vector generating unit 530 may determine a movement displacement vector of the liver serving as an object based on the magnetic resonance image of the first respiration phase and the magnetic resonance image of the second respiration phase extracted by the image extracting unit 520.

The first image registration unit 540 may register the magnetic resonance image of the first respiration phase extracted by the image extracting unit 520 to a computerized tomography image of the first respiration phase of the liver serving as an object.

The image generating unit 550 may include the displacement vector applying unit 551 and generate a computerized tomography image of the second respiration phase of the liver serving as an object from the magnetic resonance image data selected by the data selecting unit 510. In this case, the displacement vector applying unit 551 may apply the movement displacement vector of the liver serving as an object determined by the displacement vector generating unit 530 to the computerized tomography image of the first respiration phase of the object.

The second image registration unit 560 may perform registration of the ultrasound image and the computerized tomography image of the liver serving as an object based on the computerized tomography image of the first respiration phase of the liver serving as an object that is input through the input unit 155 or received through the communication unit 600 and the computerized tomography image of the second respiration phase generated by the image generating unit 550.

The display unit 160 may display the magnetic resonance image of the object selected by the data selecting unit 510 under control of the processor 410, display the magnetic resonance images of the first respiration phase and the second respiration phase of the object extracted by the image extracting unit 520, and display the image registered by the first image registration unit 540 and the computerized tomography image of the second respiration phase of the liver generated by the image generating unit 550. Finally, the display unit 160 may display the registration image of the computerized tomography image and the ultrasound image of the liver that is registered by the second image registration unit 560. This registration image may be displayed on the display unit 160 included in the separate image processing apparatus 501 or displayed on the display unit 160 included in the ultrasound imaging apparatus 100.

Figure 8:
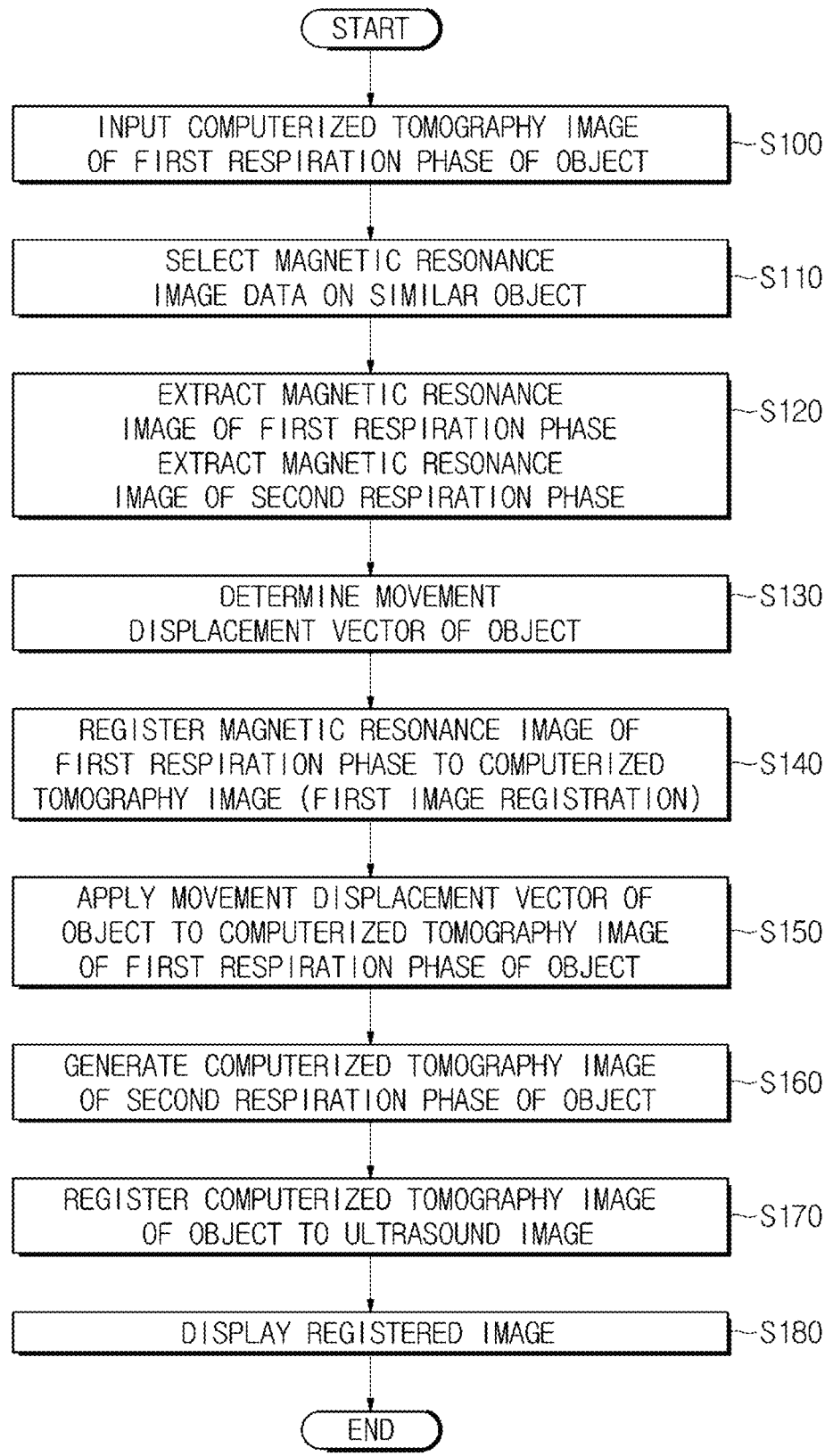
FIG. 8 is a flowchart illustrating an image processing method according to an exemplary embodiment.

FIG. 8 is a flowchart illustrating an image processing method according to an exemplary embodiment.

As illustrated in FIG. 8, the image processing method according to an exemplary embodiment will be described in detail with reference to FIGS. 9 to 14.

The user may input the computerized tomography image data of the first respiration phase of the object imaged by a computerized tomography imaging apparatus through the input unit 155 of the image processing apparatus 501 in operation S100.

As described above, the object may be a human's organ such as a liver, a heart, and a lung. For convenience of description, while the image processing method according to an exemplary embodiment exemplifies a case in which the object is the liver, the exemplary embodiments are not limited thereto. Also, as described above, the first respiration phase is a respiration phase in which the user takes a breath, that is, during inspiration (inhalation). In this case, as illustrated in FIG. 6, the liver has a relatively pressed shape. The computerized tomography image of the first respiration phase of the liver may be directly input through the input unit 155 or image data may be received from the computerized tomography imaging apparatus through the communication unit 600. The image data received through the communication unit 600 may be stored in the storage unit 700 and transmitted to the processor 410.

Figure 9:
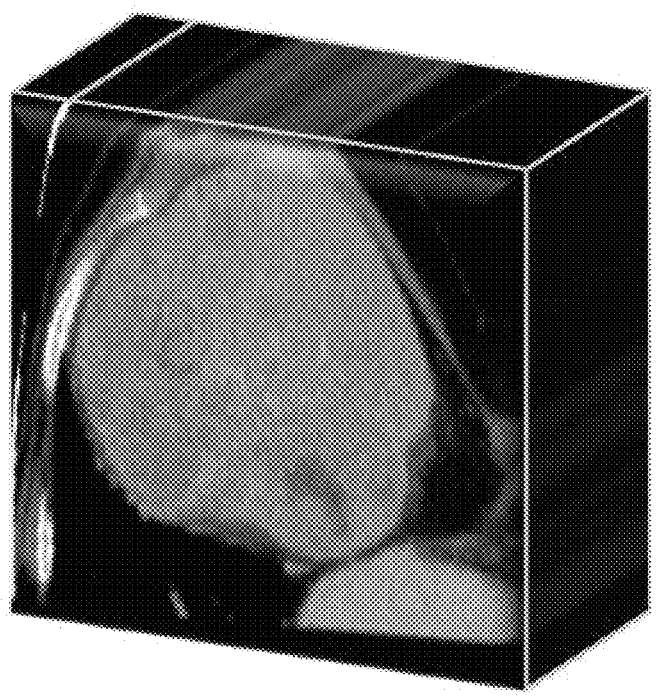
FIG. 9 shows computerized tomography image data of a first respiration phase of a liver serving as an object.

FIG. 9 shows computerized tomography image data of a first respiration phase of a liver serving as an object.

As illustrated in FIG. 9, an area displayed as gray corresponds to the liver serving as an object and 3D volume data of the computerized tomography image is represented.

As described above, when computerized tomography is performed, since the object is imaged while the user inhales, the computerized tomography image of the first respiration phase refers to an image of the liver that is relatively pressed and refers to the liver illustrated in FIG. 6A.

The data selecting unit 510 may select magnetic resonance image data of an object similar to the object corresponding to the computerized tomography image data of the first respiration phase that is input through the input unit 155 or received by the communication unit 600 in operation S110.

As the computerized tomography image data of the first respiration phase, magnetic resonance image data of the liver similar to the input image data of the liver is selected so that magnetic resonance image data is used as sample data and computerized tomography image data during expiration (exhalation) is generated. Data that can be used as sample data is not limited to being magnetic resonance image data, but magnetic resonance image data is exemplified in an exemplary embodiment.

The magnetic resonance image data of the object is data of a plurality of objects imaged by the magnetic resonance imaging apparatus, is generally stored in the storage unit 700 of the image processing apparatus 501, and may be input through the input unit 155 after the computerized tomography image data of the first respiration phase on the object is input, or received and used from the communication unit 600.

The data selecting unit 510 includes the similarity determining unit 511, the object volume calculating unit 512, and the object weight calculating unit 513, and selects the magnetic resonance image data of the liver. When there is magnetic resonance image data of the user's object corresponding to input computerized tomography image data, the image processing method according to an exemplary embodiment may be performed using corresponding data. On the other hand, when there is no magnetic resonance image data of the object of the same user, in order to perform image processing using magnetic resonance image data of an object that is the closest to the object, a selection from the stored data is performed.

In order to determine similarity of the object, first, the similarity determining unit 511 of the data selecting unit 510 compares anatomical features of the object corresponding to computerized tomography image data and the object corresponding to the stored magnetic resonance image data. Specifically, from information on the patient's body including the liver corresponding to the object, similarity with the object corresponding to the stored magnetic resonance image data is determined. As determination criteria, information on a target patient's body including the liver serving as an object, such as a gender, an age, a body height (BH), and a body weight (BW), is used to select data of the liver that is a similar object. Additionally, information on severity of disease of the target patient may be input and magnetic resonance image data according to a phase of disease may also be selected.

When a gender, an age, a body height, a body weight, and the like serving as similarity determination criteria are similar, it may be assumed that a size of the object is similar. In the exemplified liver, sizes and volumes of the liver of the target patient and the liver corresponding to the stored magnetic resonance image data are compared to determine similar data.

As illustrated in FIG. 7, the similarity determining unit 511 of the data selecting unit 510 may compare values of a gender, an age, a body height, and a body weight of the target patient of input or received computerized tomography image data of the object and values of a person including the object stored as magnetic resonance image data and select similar data among them. Also, the object volume calculating unit 512 calculates a volume of the object input as computerized tomography image data based on the above information, and the object weight calculating unit 513 calculates a weight of the object. Based on the computed values, the similarity determining unit 511 may finally determine similarity of the input computerized tomography image data of the liver and magnetic resonance image data.

In the case of the liver, as a criterion for determining data similarity, a total liver volume (TVL) value that represents a volume of the liver may be expressed as Equation 1.

TVL=−794.41+1,267.28*BSA     [Equation 1]

A BSA value in Equation 1 represents a body surface area and is computed based on a body weight (BW) and a body height (BH) of a target patient.

As another criterion for determining data similarity, a liver weight (LW) value that represents a weight of the liver may be expressed as Equation 2.

LW=452+16.34*BW+11.85*age−166*gender     [Equation 2]

In Equation 2, as the "gender," "1" may represent a female and "0" may represent a male.

The object volume calculating unit 512 calculates the TVL value of the liver serving as an object. The object weight calculating unit 513 calculates the LW value of the liver serving as an object. Based on the calculated data, the similarity determining unit 511 determines similarity of the stored magnetic resonance image data and the input computerized tomography image data of the liver.

Figure 10:
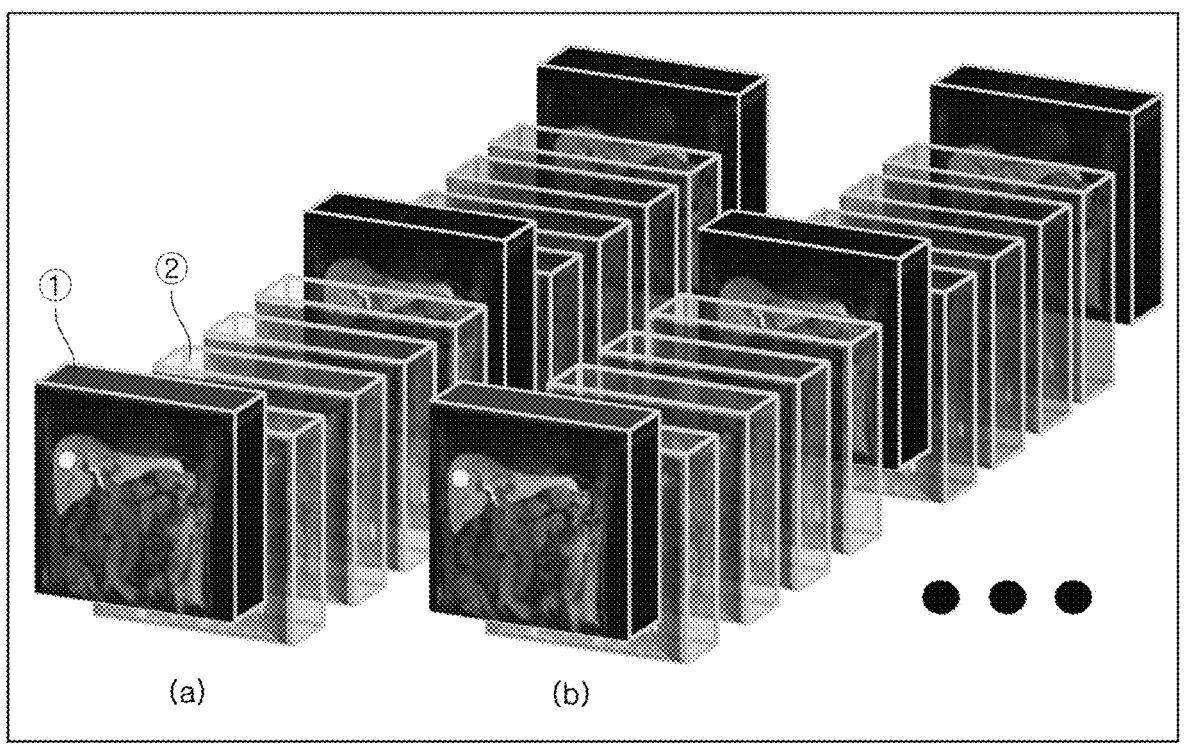
FIG. 10 is a diagram illustrating magnetic resonance image data of an object.

FIG. 10 is a diagram illustrating magnetic resonance image data of an object.

As illustrated in FIG. 10, the magnetic resonance image data of the object may be stored as a plurality of pieces of data in the storage unit 700. That is, the magnetic resonance image data of the liver serving as an object of a plurality of people or a plurality of patients may be included. This information may be displayed as magnetic resonance image data including respiration phases of inspiration (inhalation) and expiration (exhalation) of the plurality of patients. Unlike computerized tomography, since a magnetic resonance image is imaged without radiation exposure, data including several respiration phases may be generated, and since respiration phases of inhalation and exhalation are repeated over time, data may be stored as 4D data including a time domain. As illustrated in FIG. 10, (a) and (b) of FIG. 10 represent magnetic resonance image data of the liver of different target patients, ① represents magnetic resonance image data of the object during inspiration, and ② represents magnetic resonance image data of the object during expiration. According to a flow of respiration, data in which phases of ① and ② are repeated is generated. The data selecting unit 510 selects data similar to input computerized tomography image data of the liver from among a plurality of magnetic resonance image data sets represented as (a), (b), and the like.

The first respiration phase image extracting unit 521 and the second respiration phase image extracting unit 522 of the image extracting unit 520 extract image data of the first respiration phase and the second respiration phase, respectively, from magnetic resonance image data of the respiration phase of the liver selected by the data selecting unit 510 in operation S120.

As described above, in the magnetic resonance image data of the respiration phase of the liver, respiration phases of inspiration and expiration are repeated. Among them, the magnetic resonance image of the first respiration phase corresponding to inspiration and the magnetic resonance image of the second respiration phase corresponding to expiration are extracted. As the data to be extracted, one piece of data of the first respiration phase and one piece of data of the second respiration phase may be extracted, or a plurality of pieces of data of the first respiration phase and a plurality of pieces of data of the second respiration phase may be extracted. As a criterion for extracting data according to the respiration phase, data for each time is determined based on a repetitive respiration period since the respiration phase occurs over time, and data of the first respiration phase and the second respiration phase may be extracted.

The displacement vector generating unit 530 determines a movement displacement vector of the liver serving as an object from magnetic resonance image data of the first respiration phase and the second respiration phase extracted by the image extracting unit 520 in operation S130.

When the first respiration phase of inhalation and the second respiration phase of exhalation are repeated, a shape of the liver is deformed. Therefore, the displacement vector generating unit 530 may calculate a degree of deformation or a direction of deformation as a vector.

FIG. 11 shows movement of coordinates for calculating a movement displacement vector in a first respiration phase and a second respiration phase of the liver.

As illustrated in FIG. 11, (a) of FIG. 11 represents the magnetic resonance image of the first respiration phase of the liver extracted by the first respiration phase image extracting unit 521, and (b) of FIG. 11 represents the magnetic resonance image of the second respiration phase of the liver extracted by the second respiration phase image extracting unit 522.

In the magnetic resonance image of the first respiration phase, the liver has a slightly pressed shape. In the magnetic resonance image of the second respiration phase, the liver has an unpressed shape. In (a) of FIG. 11, areas indicated as a triangle, an X, and a circle represent features that indicate specific points for determining a movement displacement vector from shape deformation of the liver between the first respiration phase and the second respiration phase.

Positions of areas of a triangle, an X, and a circle of the liver during inspiration move to areas of a triangle, an X, and a circle of the liver during expiration. This reflects movement of points in a surface of the liver while the liver is pressed or unpressed according to the respiration phase.

As a specific method of the displacement vector generating unit 530 determining a movement displacement vector of the liver, a concept of non-rigid registration based on features is used. First, features are extracted from the magnetic resonance image of the first respiration phase and the magnetic resonance image of the second respiration phase (e.g., feature extraction), and then a vector format may be described using the extracted features (e.g., feature descriptor). Based on distances between features described in the vector format, among features within a predetermined distance, the nearest neighbors are determined to correspond to each other. As a criterion of the nearest neighbor to be determined to correspond, when a distance between features within a predetermined area is a specific threshold distance or less, and a ratio of the closest position to the next closest position is a specific ratio or less, correspondence may be determined. Next, a deformable mesh model is applied, and deformable mesh energy is applied when a displacement vector is calculated. The reason why deformable mesh energy is applied is because, since a mesh structure has an energy type that is less variable than that of a free energy state, in order to calculate an appropriate displacement vector of an entire image domain based on feature correspondence, free-form deformation based on B-splines is used. In a free-form deformation technique, a feature extracting method in which lattices of control points forming B-splines are moved to deform an object is unnecessary. Since the technique has high degrees of freedom, it is appropriate to model complex local deformation. The free-form deformation technique is disclosed in Non-Patent Document, D. Rueckert et al., "Nonrigid registration using free-form deformations: Application to breast MR images," IEEE Trans. Medical Imaging, vol. 18, pp. 712-721, 1999.

Therefore, energy (e.g., feature correspondence energy) of correspondence between features and deformable mesh energy are applied to find energy that appropriately satisfies both. An energy function of a model is defined using correspondence with a displacement of lattice points of the deformable mesh model. A solution of the displacement vector that minimizes this function value may be computed using a preconditioned nonlinear conjugate gradient (PCG) method. According to the above-described method, the displacement vector may be calculated from the magnetic resonance image of the first respiration phase and the magnetic resonance image of the second respiration phase illustrated in FIG. 11. The method of calculating the displacement vector based on features in this manner is a technique that is generally used.

The first image registration unit 540 may register the input computerized tomography image of the first respiration phase of the liver serving as an object to the magnetic resonance image of the first respiration phase extracted by the image extracting unit 520. That is, registration may be performed such that, by matching coordinates of the computerized tomography image and the magnetic resonance image, the computerized tomography image may be observed or searched for according to coordinates or a position of the magnetic resonance image.

FIG. 12 shows a concept of registration of a computerized tomography image of a first respiration phase and a magnetic resonance image of the first respiration phase of the liver according to an exemplary embodiment.

As illustrated in FIG. 12, (a) of FIG. 12 represents the extracted magnetic resonance image of the first respiration phase, and (b) of FIG. 12 represents the input computerized tomography image of the first respiration phase. Registration is performed based on each point of the magnetic resonance image and the computerized tomography image of the liver. As a result, coordinates of the input computerized tomography image of the first respiration phase and the magnetic resonance image match on a 3D coordinate system and therefore may be identified at the same coordinates.

In this manner, the magnetic resonance image and the computerized tomography image of the first respiration phase are registered. As will be described below, this registration is performed in order to apply the movement displacement vector determined from the magnetic resonance image data to the computerized tomography image of the first respiration phase.

As a specific method of the first image registration unit 540 registering the computerized tomography image of the first respiration phase to the magnetic resonance image of the first respiration phase, image information of a surface of the liver serving as an object is obtained and the computerized tomography image and the magnetic resonance image are registered based thereon. As an image that is imaged by injecting a contrast agent into the liver serving as an object of interest, in the computerized tomography image and the magnetic resonance image, boundaries of the liver and the lung are very clear, and therefore information on the surface of the liver may be obtained. As illustrated in (a) and (b) of FIG. 12, an area indicated by a thick line represents the surface of the liver. Therefore, rigid registration may be performed using such surface boundary information of the liver through an iterative closest point (ICP) technique. Since the computerized tomography image of the first respiration phase and the magnetic resonance image of the first respiration phase may be data of objects of different patients, information may not completely match. Accordingly, rough position registration may be performed using only a rotation and translation method without deformation inside the object through rigid registration. As described above, the computerized tomography image of the first respiration phase and the magnetic resonance image of the first respiration phase may be registered using a generally used registration technique in operation S140.

The displacement vector applying unit 551 in the image generating unit 550 applies the movement displacement vector of the liver generated by the displacement vector generating unit 530 to the computerized tomography image of the first respiration phase of the liver in operation S150, and may generate the computerized tomography image of the second respiration phase of the object in operation S160.

The displacement vector applying unit 551 may apply the displacement vector determined by the displacement vector generating unit 530 from the magnetic resonance image data of the first respiration phase and the magnetic resonance image data of the second respiration phase to the computerized tomography image data of the first respiration phase.

FIG. 13 shows generation of a computerized tomography image of the second respiration phase of the liver by applying a displacement vector determined from magnetic resonance image data of the liver to computerized tomography image data of the first respiration phase.

As illustrated in FIG. 11, the movement displacement vector determined from the magnetic resonance image data of the first respiration phase and the second respiration phase of the liver may be applied to the computerized tomography image data of the liver illustrated in FIG. 13. The computerized tomography image of the second respiration phase may be generated using a method in which, under control of the processor 410, the displacement vector applying unit 551 reflects the movement displacement vector determined by the displacement vector generating unit 530 to points of a triangle, an X, and a circle of the computerized tomography image data of the first respiration phase, and corresponding points of the computerized tomography image data of the second respiration phase are found, as shown in (a) and (b) of FIG. 13. In this case, the above-described deformable mesh model may be applied.

Finally, the second image registration unit 560 may register the computerized tomography image to the ultrasound image of the liver based on the computerized tomography image of the first respiration phase of the liver serving as an object and the computerized tomography image of the second respiration phase of the liver generated by the image generating unit 550 in operation S170). In the registration image, coordinates or positions of both images match to be observed from the same viewpoint. Images may be separately displayed and observed at the same time, or images may be displayed in an overlapping manner and observed in one image at the same time.

According to the above computerized tomography image generation of the second respiration phase, one computerized tomography image of the second respiration phase may be generated from one computerized tomography image of the first respiration phase. However, further, from the input computerized tomography image of the first respiration phase and the generated computerized tomography image of the second respiration phase, consecutive images to be registered to the ultrasound image of the liver may be generated.

FIG. 14 shows an image that is obtained by registering a computerized tomography image to an ultrasound image according to an exemplary embodiment.

As shown in FIG. 14, (a) of FIG. 14 represents an ultrasound image, (b) of FIG. 14 represents a computerized tomography image, and (c) of FIG. 14 represents an image in which both images are registered. As shown in (c) of FIG. 14, when the ultrasound image and the computerized tomography image are displayed in an overlapping manner, the images may be distinguishably displayed with different colors or brightness. Since the ultrasound image and the computerized tomography image may be observed from the same position and the same viewpoint through the registration image, it may be effective to observe lesions such as cancer.

The display unit 160 may display a final image in which the ultrasound image and the computerized tomography image are registered in operation S180. As described above, on the display unit 160, both of the ultrasound image and the computerized tomography image may be registered and displayed on different screens at the same time for observation, or may be displayed in an overlapping manner and observed in one screen.

Figure 15:
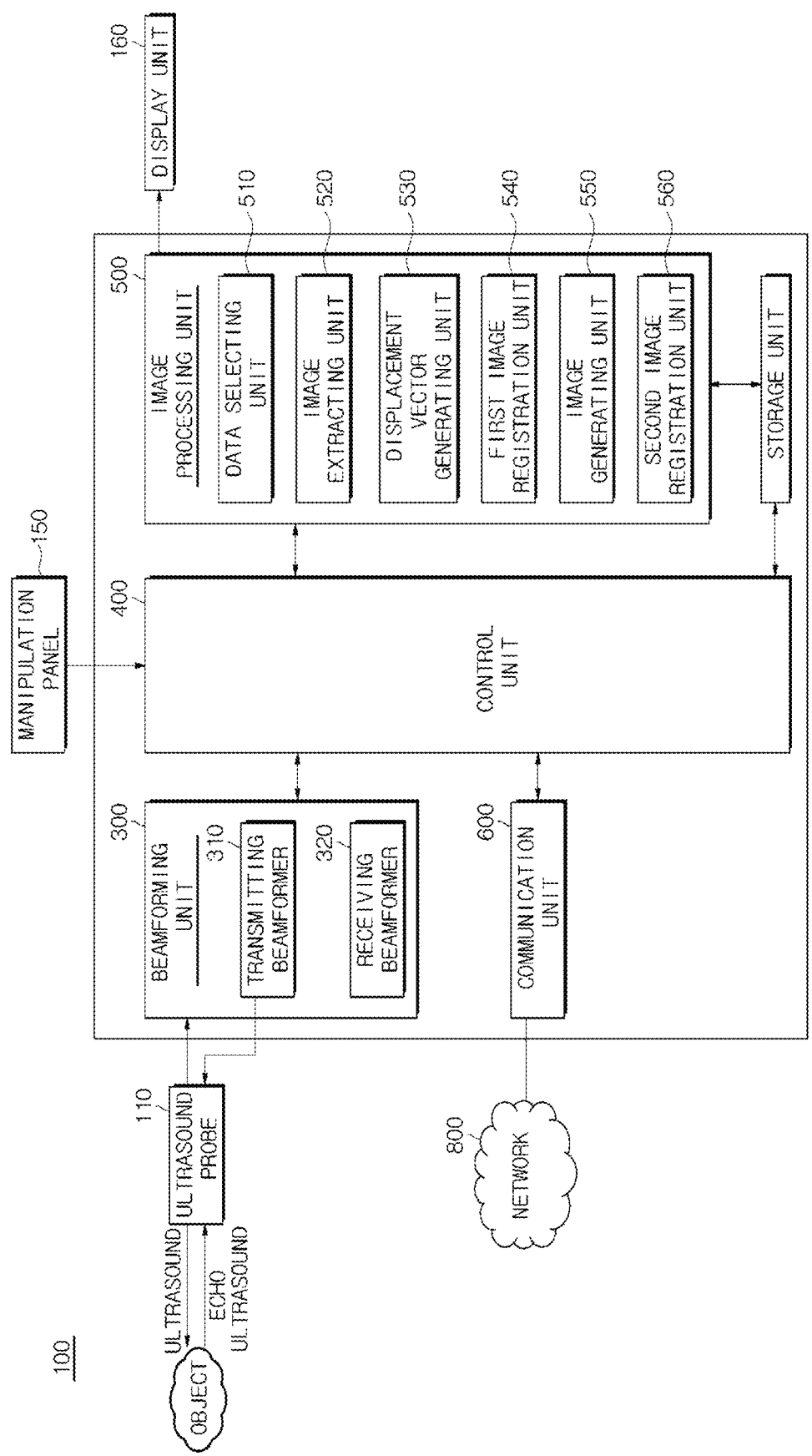
FIG. 15 is a control block diagram of an ultrasound imaging apparatus according to an exemplary embodiment.

FIG. 15 is a control block diagram of an ultrasound imaging apparatus according to an exemplary embodiment.

The image processing apparatus may be implemented as a separate apparatus including software such as the processor 410 as illustrated in FIG. 7, or implemented as an image processing unit 500 in the ultrasound imaging apparatus as illustrated in FIG. 15.

As illustrated in FIG. 15, the ultrasound imaging apparatus 100 according to an exemplary embodiment may include the ultrasound probe 110, a beamforming unit 300 (e.g., beamformer), a control unit 400 (e.g., controller), the image processing unit 500 (e.g., image processor), the communication unit 600 (e.g., communicator), and the storage unit 700 (e.g., storage).

The ultrasound probe 110 may be variously implemented within the scope of a technique for obtaining volume data of the object. For example, when elements of the ultrasound probe 110 have a 1D array, the ultrasound probe 110 may obtain volume data according to a freehand method. Also, without the user's manipulation, the ultrasound probe 110 may obtain volume data according to a mechanical method. On the other hand, when elements of the ultrasound probe 110 have a 2D array, the ultrasound probe 110 may obtain volume data by controlling elements.

The beamforming unit 300 includes a transmitting beamformer 310 and a receiving beamformer 320, interconverts an analog signal and a digital signal, and may adjust a time difference of ultrasounds transmitted from at least one transducer (T) or ultrasounds received from at least one transducer. As illustrated in FIG. 2, the beamforming unit 300 may be included in the main body of the ultrasound imaging apparatus 100, or may be provided in the ultrasound probe 110 and perform a function thereof.

As described in FIG. 7, the communication unit 600 may be connected to another apparatus and transmit and receive data to and from the connected apparatus. In particular, the communication unit 600 may be connected to another apparatus connected to a network 800, receive image data of the liver serving as an object imaged by the computerized tomography apparatus, receive body information or anatomical features of a patient input to another apparatus, and receive the magnetic resonance image data of the liver imaged by the magnetic resonance imaging apparatus. As described above, data may be directly input through the input unit 155 and data received by the communication unit 600 may also be used. The communication unit 600 may transmit the received data to the control unit 400, store the data in the storage unit 700, and use the data for first image registration and second image registration according to an exemplary embodiment.

The control unit 400 may store the data received from the communication unit 600 in the storage unit 700 or transmit the data to the image processing unit 500, and may control image processing of the ultrasound image that is performed by the image processing unit 500. Also, the control unit 400 may perform control such that the display unit 160 displays the registration image of the computerized tomography image and the ultrasound image generated by the image processing unit 500.

The image processing unit 500 may include the data selecting unit 510, the image extracting unit 520, the displacement vector generating unit 530, the first image registration unit 540, the image generating unit 550, and the second image registration unit 560. According to an exemplary embodiment, the image processing unit 500 registers the computerized tomography image of the object to the ultrasound image of the object based on the computerized tomography image of the first respiration phase of the object and magnetic resonance image data of an object similar to the object. In this case, the image processing unit 500 may correspond to one or a plurality of processors. The processor may be implemented as an array of a plurality of logic gates, or implemented as a combination of a general purpose microprocessor and a memory in which a program that can be executed in the microprocessor is stored. For example, the image processing unit 500 may be implemented as a general purpose GPU. Since components included in the image processing unit 500 have been described with reference to FIGS. 7 to 8, redundant descriptions thereof will be omitted.

The storage unit 700 may store data used for image registration according to an exemplary embodiment. The computerized tomography image data and the magnetic resonance image data of the liver serving as an object may be stored. Image data may be directly input through the manipulation panel 150 and received from another apparatus through the communication unit 600. The data stored in the storage unit 700 may be transmitted to the control unit 400, transmitted to the image processing unit 500, and used for image generation and image registration.

The storage unit 700 may include, for example, a high-speed random access memory, a magnetic disk, an SRAM, a DRAM, and a ROM, but the exemplary embodiments are not limited thereto. Also, the storage unit 700 may be detachable from the ultrasound imaging apparatus 100. The storage unit 700 may include, for example, a compact flash (CF) card, a secure digital (SD) card, a smart media (SM) card, a multimedia card (MMC), or a memory stick, but the present invention is not limited thereto. Also, the storage unit 700 may be provided outside the ultrasound imaging apparatus 100 and transmit or receive data to or from the ultrasound imaging apparatus 100 via wired or wireless communication.

The manipulation panel 150 may input data related to the ultrasound imaging apparatus 100 according to an exemplary embodiment. Data of the computerized tomography image of the liver serving as an object may be input through the manipulation panel 150, and the user may input the computerized tomography image of the liver during inspiration. Also, the magnetic resonance image data of the liver serving as an object may be input through the manipulation panel 150. Since magnetic resonance image data of the liver is different for each person and types of information are various, data of the object obtained from the magnetic resonance imaging apparatus may be input and used to obtain data of the object having information similar to that of a target patient. Also, information on the patient's body including the object may be input through the manipulation panel 150. In addition to the above-described content, data to be used by the methods and apparatuses according to exemplary embodiments may be input.

As described in FIGS. 7 to 8, under control of the control unit 400, the display unit 160 may display the magnetic resonance image of the object selected by the data selecting unit 510, display the magnetic resonance image of the first respiration phase and the second respiration phase of the object extracted by the image extracting unit 520, and display the image registered by the first image registration unit 540 and the computerized tomography image of the second respiration phase of the liver generated by the image generating unit 550. Finally, the display unit 160 may display the registration image of the computerized tomography image and the ultrasound image of the liver that is registered by the second image registration unit 560. In this case, the registered computerized tomography image and ultrasound image may be displayed on different screens or displayed together in one screen at the same time.

According to the image processing apparatus, the image processing method, and the ultrasound imaging apparatus having an image processing apparatus, a displacement vector of the MR image may be obtained in advance, and therefore efficiency increases. Since most procedures are performed automatically or semi-automatically, additional processes are unnecessary. Also, since the CT image is not directly registered to the US image having low image quality and registration information between MR images having high image quality is used, a decrease in registration errors may be expected. When a simple and fast registration technique such as rigid registration is used later, it is possible to complete registration between the CT image and the US image with high precision.

As described above, exemplary embodiments of the image processing apparatus, the image processing method, and the ultrasound imaging apparatus having an image processing unit have been described with reference to the exemplified drawings. Examples of the image processing apparatus, the image processing method, and the ultrasound imaging apparatus having an image processing unit are not limited thereto and the above-described exemplary embodiments are only examples in all aspects. Therefore, it will be understood by those skilled in the art that the exemplary embodiments may be performed in other concrete forms without changing the technological scope and essential features. Therefore, the scope of the exemplary embodiments is defined not by the detailed description but by the appended claims. All modifications and equivalents that fall within the scope of the appended claims will be construed as being included in the exemplary embodiments.

What is claimed is:

1. An image processing apparatus, comprising:
   an input device configured to receive a computerized tomography image of an object during a first respiration phase of a patient, wherein the object is an internal organ of the patient; and
   at least one processor configured to:
   select magnetic resonance image data similar to the object from among magnetic resonance image data of a plurality of additional objects from a plurality of patients other than the patient,
   extract a magnetic resonance image of the first respiration phase and a magnetic resonance image of a second respiration phase based on the magnetic resonance image data similar to the object, and
   generate a simulated computerized tomography image of the object during the second respiration phase of the patient based on the selected magnetic resonance image data,
   wherein the at least one processor is further configured to determine similarity by comparing anatomical features of the object and anatomical features of the plurality of additional objects from a plurality of patients other than the patient stored in the magnetic resonance image data, and to select magnetic resonance image data based on the determined similarity,
   wherein the anatomical features comprise a volume and a weight of the object, and
   wherein the at least one processor is further configured to determine similarity by comparing body features of the patient to body features of the plurality of patients other than the patient, the body features comprising at least one from among gender, age, body height, or body weight.

2. The image processing apparatus according to claim 1, wherein the computerized tomography image of the object during the first respiration phase is a computerized tomography image of the object during inhalation, and
   the simulated computerized tomography image of the object during the second respiration phase is a simulated computerized tomography image of the object during exhalation.

3. The image processing apparatus according to claim 1, further comprising a storage configured to store 4D magnetic resonance image data of the object.

4. The image processing apparatus according to claim 1, wherein:
   the at least one processor is further configured to register the extracted magnetic resonance image of the first respiration phase to the computerized tomography image of the object during the first respiration phase.

5. The image processing apparatus according to claim 1, wherein the at least one processor is further configured to determine a movement displacement vector of the object based on the extracted magnetic resonance image of the first respiration phase and the extracted magnetic resonance image of the second respiration phase, and
   wherein the at least one processor is further configured to apply the determined movement displacement vector of the object to the computerized tomography image of the object during the first respiration phase.

6. The image processing apparatus according to claim 1, wherein:
   the at least one processor is further configured to register a computerized tomography image of the object to an ultrasound image of the object based on the computerized tomography image of the object during the first respiration phase of the patient and the simulated generated computerized tomography image of the object during the second respiration phase of the patient.

7. The image processing apparatus according to claim 1, wherein the at least one processor is further configured to determine a movement displacement vector of the object based on image features of the extracted magnetic resonance image of the first respiration phase and image features of the extracted magnetic resonance image of the second respiration phase by using non-rigid registration.

8. The image processing apparatus according to claim 1, wherein the body features comprise gender, age, body height, and body weight.

9. An image processing method, comprising:
receiving a computerized tomography image of an object during a first respiration phase of a patient, wherein the object is an internal organ of the patient;
selecting magnetic resonance image data similar to the object from among magnetic resonance image data of a plurality of additional objects from a plurality of patients other than the patient;
extracting a magnetic resonance image of the first respiration phase and a magnetic resonance image of a second respiration phase based on the magnetic resonance image data similar to the object; and
generating a simulated computerized tomography image of the object during the second respiration phase of the patient based on the selected magnetic resonance image data,
wherein the selecting of the magnetic resonance image data similar to the object comprises comparing anatomical features of the object and anatomical features of the plurality of additional objects from the plurality of patients other than the patient stored in the magnetic resonance image data, and selecting magnetic resonance image data based on the comparing,
wherein the anatomical features comprise a volume and a weight of the object, and
wherein the selecting of the magnetic resonance image data similar to the object comprises comparing body features of the patient to body features of the plurality of patients other than the patient, the body features comprising at least one from among gender, age, body height, or body weight.

10. The image processing method according to claim 9,
wherein the computerized tomography image of the object during the first respiration phase is a computerized tomography image of the object during inhalation, and
the simulated computerized tomography image of the object during the second respiration phase is a computerized tomography image of the object during exhalation.

11. The image processing method according to claim 9, further comprising:
registering the extracted magnetic resonance image of the first respiration phase to the computerized tomography image of the object during the first respiration phase.

12. The image processing method according to claim 9, further comprising determining a movement displacement vector of the object based on the extracted magnetic resonance image of the first respiration phase and the extracted magnetic resonance image of the second respiration phase,
wherein the generating of the simulated computerized tomography image of the object during the second respiration phase comprises applying the determined movement displacement vector of the object to the computerized tomography image of the object during the first respiration phase.

13. The image processing method according to claim 9, further comprising:
registering a computerized tomography image of the object to an ultrasound image of the object based on the computerized tomography image of the object during the first respiration phase and the generated simulated computerized tomography image of the object during the second respiration phase.

14. The image processing method according to claim 9, further comprising
determining a movement displacement vector of the object based on image features of the extracted magnetic resonance image of the first respiration phase and image features of the extracted magnetic resonance image of the second respiration phase by using non-rigid registration.

15. The image processing method according to claim 9, wherein the body features comprise gender, age, body height, and body weight.

16. An ultrasound imaging apparatus, comprising:
an ultrasound probe configured to obtain an ultrasound image signal of an object;
an image processor configured to generate an ultrasound image of the object based on the ultrasound image signal; and
a communicator configured to receive a computerized tomography image of the object during a first respiration phase of a patient and magnetic resonance image data of a plurality of additional objects from a plurality of patients other than the patient, wherein the object is an internal organ of the patient,
wherein the image processor is configured to select magnetic resonance image data similar to the object from among the magnetic resonance image data of the plurality of additional objects from the plurality of patients other than the patient, and extract a magnetic resonance image of the first respiration phase and a magnetic resonance image of a second respiration phase based on the magnetic resonance image data similar to the object,
wherein the image processor is further configured to generate a simulated computerized tomography image of the object during the second respiration phase of the patient, and register a computerized tomography image of the object to the ultrasound image of the object based on the computerized tomography image of the object during the first respiration phase, the simulated computerized tomography image of the object during the second respiration phase, and the magnetic resonance image data similar to the object from among the plurality of additional objects from the plurality of patients other than the patient,
wherein the image processor is further configured to determine similarity by comparing anatomical features of the object and anatomical features of the plurality of additional objects from the plurality of patients other than the patient stored in the magnetic resonance image data, and to select magnetic resonance image data based on the determined similarity,
wherein the anatomical features comprise a volume and a weight of the object, and
wherein the image processor is further configured to determine similarity by comparing body features of the patient to body features of the plurality of patients other than the patient, the body features comprising at least one from among gender, age, body height, or body weight.

17. The ultrasound imaging apparatus according to claim 16, further comprising:
a display configured to display the registered computerized tomography image of the object and the ultrasound image of the object.

18. The ultrasound imaging apparatus according to claim 16, further comprising:
a storage configured to store the received computerized tomography image of the object during the first respiration phase and the magnetic resonance image data similar to the object.

19. The ultrasound imaging apparatus according to claim 16,
wherein the image processor is further configured to determine a movement displacement vector of the object based on image features of the extracted magnetic resonance image of the first respiration phase and image features of the extracted magnetic resonance image of the second respiration phase, by using non-rigid registration.

20. The ultrasound imaging apparatus according to claim 16,
wherein the body features comprise gender, age, body height, and body weight.

* * * * *